United States Patent
Bhattacherjee et al.

(10) Patent No.: US 12,109,192 B2
(45) Date of Patent: Oct. 8, 2024

(54) ORGANIC ACID ADDITION SALTS OF S-PINDOLOL

(71) Applicant: ACTIMED THERAPEUTICS LTD, Ascot (GB)

(72) Inventors: Robin Chandra Bhattacherjee, Bedford (GB); Andrew Justin Stewart Coats, Richmond (AU); Elaine Morten, Long Hanborough (GB); Ronnie Maxwell Lawrence, Upper Gravenhurst (GB); Jaclyn Raeburn, Glasgow (GB); Kiara Marissa Lobato, Edinburgh (GB); Jonathan James Loughrey, Edinburgh (GB)

(73) Assignee: ACTIMED THERAPEUTICS LTD, Ascot (GB)

( * ) Notice: Subject to any disclaimer, the term of this patent is extended or adjusted under 35 U.S.C. 154(b) by 151 days.

(21) Appl. No.: 17/995,621

(22) PCT Filed: Mar. 31, 2021

(86) PCT No.: PCT/GB2021/050799
§ 371 (c)(1),
(2) Date: Oct. 6, 2022

(87) PCT Pub. No.: WO2021/205144
PCT Pub. Date: Oct. 14, 2021

(65) Prior Publication Data
US 2023/0190706 A1  Jun. 22, 2023

(30) Foreign Application Priority Data
Apr. 7, 2020 (GB) .................................. 2005112

(51) Int. Cl.
*A61K 31/404* (2006.01)
*A61K 31/192* (2006.01)
*A61K 31/194* (2006.01)

(52) U.S. Cl.
CPC .......... *A61K 31/404* (2013.01); *A61K 31/192* (2013.01); *A61K 31/194* (2013.01)

(58) Field of Classification Search
CPC ............................ A61K 31/404; C07D 209/32
See application file for complete search history.

(56) References Cited

U.S. PATENT DOCUMENTS

| | | | |
|---|---|---|---|
| 3,471,515 A | 10/1969 | Troxler et al. | |
| 4,767,784 A | 8/1988 | Zölss et al. | |
| 5,484,776 A | 1/1996 | Racz et al. | |
| 5,985,317 A | 11/1999 | Venkateshwaran et al. | |
| 2019/0046476 A1* | 2/2019 | Anker | A61P 21/00 |

FOREIGN PATENT DOCUMENTS

| | | |
|---|---|---|
| EP | 0316168 B1 | 9/1992 |
| GB | 1418288 A | 12/1975 |
| JP | 01-287064 A | 11/1989 |
| WO | 0021509 A2 | 4/2000 |
| WO | 0024386 A1 | 5/2000 |
| WO | 2008068477 A1 | 6/2008 |
| WO | 2010125348 A1 | 11/2010 |
| WO | 2014016585 A1 | 1/2014 |
| WO | 2014138806 A1 | 9/2014 |
| WO | 2014138814 A1 | 9/2014 |
| WO | 2017144977 A1 | 8/2017 |

OTHER PUBLICATIONS

Bredikhin, A.A., et al., "Synthesis and crystal structure of (S)-pindolol," Tetrahedron: Asymmetry, vol. 28, 2017 (Available online Mar. 6, 2017), pp. 442-446.
Caira, M.R., "Crystalline Polymorphism of Organic Compounds," Topics in Current Chemistry, vol. 198, 1998 (First online Jan. 1, 1999), pp. 163-208.
Castro-Tavares, J., "A comparison between the Influence of Pindolol and Propranolol on the Response of Plasma Potassium to Catecholamines," Arzneimittel-Forschung, vol. 26, No. 2, Feb. 1, 1976, pp. 238-241.
El Deeb, S., et al., "Strategies in method development to quantify enantiomeric impurities using CE," Electrophoresis, vol. 29, No. 17, Aug. 2008 (First Published Sep. 19, 2008), pp. 3552-3562.
Ferry, L.L., "Theoretical model of iontophoresis utilized in transdermal drug delivery," Pharmaceutica Acta Helvetiae, vol. 70, No. 4, Dec. 1995, pp. 279-287.
Hager, D.F., et al., "Evaluation of a cultured skin equivalent as a model membrane for iontophoretic transport," Journal of Controlled Release, vol. 30, No. 2, May 1994, pp. 117-123 (8 pages).
Himori, N., et al., "Analysis of β-adrenoceptors mediating renin release produced by isoproterenol in conscious dogs," American Journal of Physiology—Renal Physiology, vol. 238, No. 5, May 1980, pp. F387-F393.
Ishida, H., et al., "Local Anesthetic Activity of β-Adrenergic Blocking Drugs in the Crayfish Giant Axon, with Reference to Calcium Ion," The Japanese Journal of Pharmacology, vol. 30, No. 5, 1980 (Accepted Mar. 31, 1980), pp. 607-619.
Issa, Y.M., et al., "Conductometric Titration of Pindolol and Propranolol Using Ammonium Reineckate and Potassium Tetracyanonickelate," Mikrochimica Acta, vol. 118, Nos. 1-2, Mar. 1995, pp. 85-91.
Iwamura, M., et al., "Drug-Induced Inhibition of Guinea Pig Platelet Aggregation Unrelated to Their β-Adrenolytic Actions," The Japanese Journal of Pharmacology, vol. 33, No. 1, Feb. 1983, pp. 219-226.
Jakobs, K.H., et al., "[$^3$H]Dihydroergonine Binding to α-Adrenergic Receptors in Human Platelets," Klinische Wochenschrift, vol. 56, No. 1, 1978, pp. 139-145.

(Continued)

*Primary Examiner* — James D. Anderson
(74) *Attorney, Agent, or Firm* — MH2 Technology Law Group, LLP

(57) ABSTRACT

The invention relates to a pharmaceutically acceptable acid addition salt of: (i) S-pindolol; and (ii) an organic acid, wherein the organic acid has: a pKa1 of greater than or equal to 2.5; and a chemical formula of $C_xH_y(CO_2H)_z$, where x is from 1 to 10, y is from 2 to 20 and z is 1 or 2. The pharmaceutically acceptable acid addition salt is useful in treating conditions such as cachexia, sarcopenia, a neuromuscular disorder and muscle weakness.

11 Claims, 11 Drawing Sheets

(56) References Cited

OTHER PUBLICATIONS

Kaumann, A.J., et al., "A Comparison of the Influence of N-Isopropyl and N-Tert Butyl Substituents on the Affinity of Ligands for Sinoatrial β-Adrenoceptors in Rat Atria and β-Adrenoceptors Coupled to the Adenylyl Cyclase in Kitten Ventricle," Naunyn-Schmiedeberg's Archives of Pharmacology, vol. 307, No. 1, May 1979, pp. 1-8.

Kaumann, A.J., et al., "Mode of action of (−)-pindolol on feline and human myocardium," British Journal of Pharmacology, vol. 89, No. 1, Jan. 1986, pp. 207-218.

Khalil, S., et al., "Indirect atomic absorption spectrometric determination of pindolol, propranolol and levamisole hydrochlorides based on formation of ion-associates with ammonium reineckate and sodium cobaltinitrite," Journal of Pharmaceutical and Biomedical Analysis, vol. 22, No. 2, Mar. 2000, pp. 235-240.

Khalil, S., et al., "Indirect atomic absorption spectrometric determination of pindolol, propranolol and levamisole hydrochlorides based on formation of ion associates with manganese thiocyanate and potassium ferricyanide," Journal of Pharmaceutical and Biomedical Analysis, vol. 22, No. 1, Mar. 2000, pp. 7-12.

Kiechel, J.R., et al., "Metabolites of Pindolol in Different Animal Species," Xenobiotica, vol. 5, No. 12, 1975 (Published online Oct. 14, 2008), pp. 741-754 (15 pages).

Ko, M.Y., et al., "Chiral Separation of β-Blockers after Derivatization with a New Chiral Derivatization Agent, GATC," Archives of Pharmacal Research, vol. 29, No. 11, Nov. 2006, pp. 1061-1065.

Nasa, Y., et al., "Cardioprotective effect of pindolol in ischemic-reperfused isolated rat hearts," European Journal of Pharmacology, vol. 213, No. 2, Mar. 24, 1992, pp. 171-181.

Neau, S.H., et al., "Melting point phase diagrams of free base and hydrochloride salts of bevantolol, pindolol and propranolol," International Journal of Pharmaceutics, vol. 99, Nos. 2-3, Oct. 1993, pp. 303-310.

Pietiläinen, H., et al., "HPLC Determination of Pindolol Benzoate and Pindolol 2-Methoxyphenylacetate," Journal of Liquid Chromatography & Related Technologies, vol. 19, No. 4, 1996 (Published online Aug. 15, 2006), pp. 583-591 (11 pages).

Pietiläinen, H., et al., "Synthesis and Physical Studies of the Organic Salts of Pindolol: Pindolol Benzoate and Pindolol 2-Methoxyphenylacetate," Drug Development and Industrial Pharmacy, vol. 22, No. 11, 1996 (Published online Oct. 20, 2008), pp. 1063-1073.

Quiming, N.S., et al., "Retention prediction of adrenoreceptor agonists and antagonists on unmodified silica phase in hydrophilic interaction chromatography," Analytical and Bioanalytical Chemistry, vol. 388, No. 8, 2007 (Published online Jun. 22, 2007), pp. 1693-1706.

Rodgers, T., et al., "Tissue Distribution of Basic Drugs: Accounting for Enantiomeric, Compound and Regional Differences Amongst β-Blocking Drugs in Rat," Journal of Pharmaceutical Sciences, vol. 94, No. 6, Jun. 2005, pp. 1237-1248.

Skelin, I., et al., "Both acute and subchronic treatments with pindolol, a 5-$HT_{1A\ and\ \beta1}$ and $\beta_2$ adrenoceptor antagonist, elevate regional serotonin synthesis in the rat brain: An autoradiographic study," Neurochemistry International, vol. 61, No. 8, 2012 (Available online Oct. 22, 2012), pp. 1417-1423.

Suh, S.K., et al., "The Relationship of in vitro Dissolution and Intestinal Membrane Permeability with in vivo Bioavailability," Yakhak Hoeji, vol. 44, No. 5, 2000, pp. 424-431, English Abstract provided.

Szász, Gy., et al., "Optimized and Validated HPLC Methods for Compendial Quality Assessment. III. Testing of Optical Purity Applying $\alpha_1$-Acid-Glycoprotein Stationary Phase," Journal of Liquid Chromatography & Related Technologies, vol. 21, No. 16, 1998 (Published online Aug. 19, 2006), pp. 2535-2547 (14 pages).

Van Den Driessche, J. et al., "Activity of some Drugs on the Electroencephalogram of Curarized Rats during Acute and Iterative Hypercapnic Anoxia Hypotheses on Mechanisms of Action," Archives Internationales de Pharmacodynamie et de Therapie, vol. 239, No. 1, May 1, 1979, pp. 62-77.

Visken® (Pindolol) Tablets, Sandoz Pharmaceuticals, Patient Information Leaflet, Oct. 16, 2020, 2 pages.

Sotoca, Usina E. (Authorized Officer), International Search Report dated May 17, 2021, for International Application No. PCT/GB2021/050799, 3 pages.

* cited by examiner

ORGANIC ACID ADDITION SALTS OF S-PINDOLOL

CROSS-REFERENCE TO RELATED APPLICATIONS

This application is a U.S. National Stage application of PCT/GB2021/050799 filed 31 Mar. 2021, which claims priority to GB 2005112.4 filed 7 Apr. 2020, the entire disclosures of which are herein incorporated by reference.

FIELD OF THE INVENTION

The present invention relates to a salt of S-pindolol and pharmaceutical compositions comprising the salt. Medical uses of the salt are also described.

BACKGROUND OF THE INVENTION

S-pindolol is a β-adrenergic receptor antagonist and is also known as (—)-pindolol. The systematic name for S-pindolol is (2S)-1-(1H-indol-4-yloxy)-3-(propan-2-ylamino)propan-2-ol and the structure of this compound is shown below.

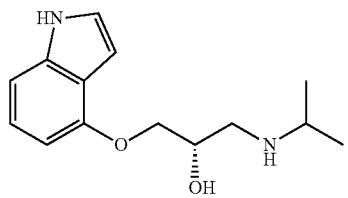 [SMILES: CC(C)NC[C@H](O)COc1cccc2[nH]ccc12]

S-pindolol has affinity for both beta-adrenergic receptors and 5-HT1 a receptors and is useful in treating a number of disorders. WO 2008/068477 A1 describes the treatment of cachexia with S-pindolol.

Pindolol is authorised for the treatment of certain conditions in the form of the racemate. It has been found that S-pindolol is the more pharmacologically active enantiomer. It is a finding of the present invention that S-pindolol has characteristics which can make it difficult to formulate as an oral medicament, for instance a tablet. In particular, S-pindolol can on occasion and under certain conditions degrade and discolour during storage.

There is a need to develop a solid form of S-pindolol which is well suited to use in the clinical context. In particular, it is desirable to develop a solid which is crystalline, stable and has a suitable colour for pharmaceutical applications.

S-pindolol tartrate is described in Kaumann et al, British Journal of Pharmacology 1986 89 (1) 207-218. S-pindolol hydrochloride is described in Japanese patent application JPH01287064 (A). The racemic benzoate salt of pindolol is described in Pietiläinen et al, Drug Development and Industrial Pharmacy, 22(11), 1063-1073 (1996).

SUMMARY OF THE INVENTION

The inventors have found that salts of S-pindolol formed with organic mono- and di-carboxylic acids having a $pK_a$ of at least 2.5 are well suited to pharmaceutical formulation. In particular, these salts have been found to be stable, crystalline and to have increased melting points compared to S-pindolol free base. Several of the S-pindolol salts also have a pure white colour which is desirable for clinical use of the solid form.

The invention provides a pharmaceutically acceptable acid addition salt of: (i) S-pindolol; and (ii) an organic acid, wherein the organic acid has: a $pK_{a1}$ of greater than or equal to 2.5; and a chemical formula of $C_xH_y(CO_2H)_z$, where x is from 1 to 10, y is from 2 to 20 and z is 1 or 2.

The invention also provides a composition comprising at least 60 wt % of the pharmaceutically acceptable acid addition salt.

Further provided by the invention is a pharmaceutical composition comprising (i) the pharmaceutically acceptable acid addition salt and (ii) a pharmaceutically acceptable excipient, carrier or diluent.

The pharmaceutically acceptable acid addition salt for use in the treatment of the human or animal body is also provided by the invention.

DETAILED DESCRIPTION OF THE INVENTION

Figure 1:
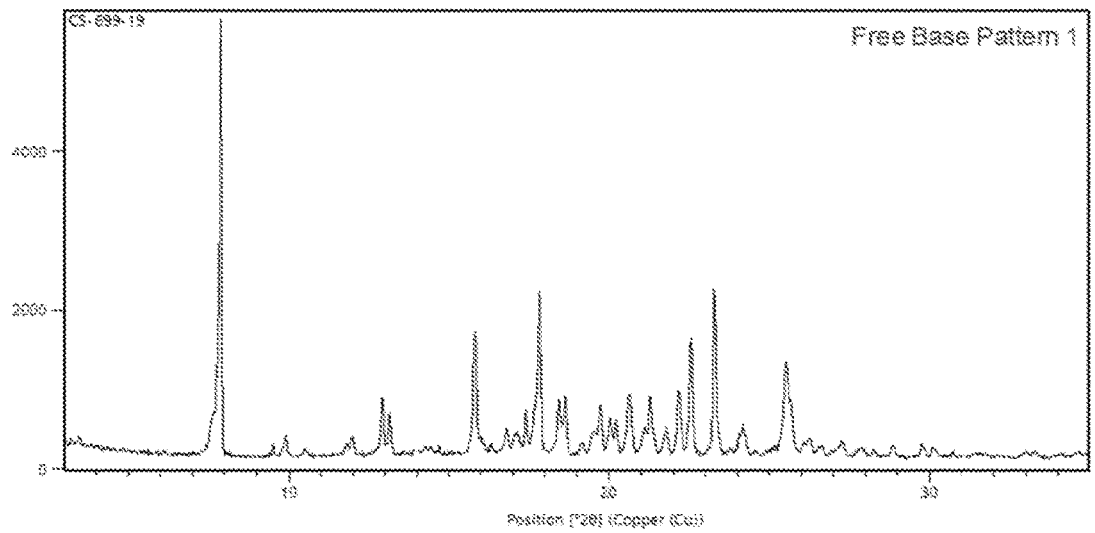
FIG. 1 shows the XRPD 2θ diffractogram of S-pindolol free base Pattern 1.

The organic acid has a $pK_{a1}$ of greater than or equal to 2.5. As such, the organic acid is a relatively weak acid. The organic acid preferably has a $pK_{ai}$ of from 3.0 to 5.0. For instance, the $pK_{ai}$ of the organic acid may be from 4.0 to 4.5. $pK_{a1}$ is the acid dissociation constant of the first proton to dissociate from the acid. For a monocarboxylic acid, $pK_{ai}$ corresponds simply to the acid dissociation constant $pK_a$. As used herein the $pK_{ai}$ values are as measured at 25° C. pKa and $pK_{ai}$ values for organic acids are readily available to the skilled person.

The organic acid has the chemical formula of $C_xH_y(CO_2H)_z$, where x is from 1 to 10, y is from 2 to 20 and z is 1 or 2. Thus, the organic acid comprises a hydrocarbyl moiety ($C_xH_y$, consisting of hydrogen and carbon) and one or two carboxylic acid groups ($CO_2H$). Typically x is from 2 to 7 and H is from 2 to 6. The $C_xH_y$ group may be an arenyl group, an alkyl group or an alkenyl group. For instance, the $C_xH_y$ group may be a divalent $C_{2-7}$ alkyl group, a divalent $C_{2-7}$ alkenyl group or a divalent phenyl group optionally substituted with one or two methyl groups.

The organic acid may, for instance, be benzoic acid, succinic acid, fumaric acid, malonic acid, acetic acid, propionic acid, glutaric acid, adipic acid, phenylacetic acid, toluic acid (including o-, m- and p-toluic acid) and naphthoic acid (including 1- and 2-naphthoic acid).

The $pK_{ai}$ of these acids are shown in the table below. Where the acid is a monocarboxylic acid, the stated $pK_{ai}$ is the $pK_a$ for that acid.

| acid | $pK_{a1}$ |
|---|---|
| benzoic acid | 4.19 |
| succinic acid | 4.21 |
| fumaric acid | 3.03 |
| malonic acid | 2.83 |
| acetic acid | 4.76 |
| propionic acid | 4.88 |
| glutaric acid | 4.34 |
| adipic acid | 4.41 |
| phenylacetic acid | 4.31 |
| toluic acid | 4-5 |
| 1-naphthoic acid | 3.67 |
| 2-naphthoic acid | 4.16 |

The structures of benzoic acid, succinic acid and fumaric acid are as follows.

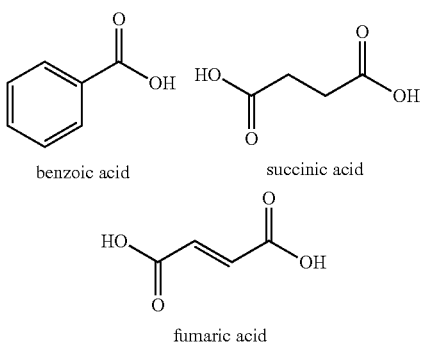

benzoic acid     succinic acid fumaric acid

Typically, the organic acid is benzoic acid or succinic acid. Preferably, the organic acid is benzoic acid.

The pharmaceutically acceptable acid addition salt is a salt of S-pindolol and therefore comprises a cation formed from S-pindolol. The cation formed from S-pindolol typically has the following structure:

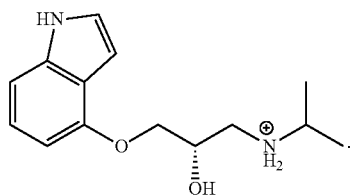 [SMILES: CC(C)[NH2+]C[C@H](O)COc1cccc2[nH]ccc12]

The enantiomeric excess of the S-enantiomer of the cation of pindolol in the pharmaceutically acceptable salt is typically at least 80%. Thus, of the cations in the salt, at least 90 mol % are typically in the S-configuration. The enantiomeric excess is typically at least 95%. The cation of S-pindolol in the pharmaceutically acceptable acid addition salt is typically substantially in S-configuration and therefore may have an enantiomeric excess of at least 99%. Enantiomeric excess may be measured by any standard technique, for instance by measuring optical rotation or using chiral high performance liquid chromatography (HPLC).

The pharmaceutically acceptable acid addition salt typically does not therefore comprise greater than 10 mol % of the R-enantiomer of pindolol or a salt comprising a cation which is a protonated R-pindolol molecule. For instance, the pharmaceutically acceptable acid addition salt is typically substantially free of the R-enantiomer of pindolol or a salt comprising a cation which is a protonated R-pindolol molecule.

The pharmaceutically acceptable acid addition salt is typically crystalline. The salt accordingly may have a three dimensional crystal structure comprising repeating unit cells. The pharmaceutically acceptable acid addition salt may be in a solid form, for instance a solid form comprising crystals or crystallites of the pharmaceutically acceptable acid addition salt.

The pharmaceutically acceptable acid salt may be in the form of a solvate. A solvate of a salt is a solid form of the salt which comprises molecules of a solvent. For instance, the salt may be a hydrate. Typically, the salt is not a solvate. For example, the pharmaceutically acceptable acid addition salt may be anhydrous.

The pharmaceutically acceptable acid addition salt typically has a melting point which is greater than the melting point of S-pindolol free base. The salt may have a melting point of greater than or equal to 100° C., for instance from 110° C. to 170° C. Typically, the salt has a melting point of 130° C. to 160° C. The melting point may, for instance, be as determined used differential scanning calorimetry (DSC).

The pharmaceutically acceptable acid addition salts may be formed by any suitable method. Typically, S-pindolol free base is treated with the organic acid in a solvent.

The solvent may be water, an alcohol (for instance ethanol or 2-propanol), an ester (for instance ethyl acetate), a ketone (for instance acetone) or an ether (for instance tetrahydrofuran (THF) or ethyl ether). The pharmaceutically acceptable acid addition salt produced may be dissolved in the solvent or may precipitate out of solution. The pharmaceutically acceptable acid addition salt may be isolated by a suitable method, for instance by filtration or by solvent evaporation.

The pharmaceutically acceptable acid addition salt may be S-pindolol benzoate. The salt may accordingly comprise the cation derived from S-pindolol and a benzoate anion. The stoichiometry of the cation and anion is typically about 1:1, for instance from 0.9:1.0 to 1.1:1.0 (i.e. for each mole of the anion, there may be from 0.9 to 1.1 moles of the cation). Preferably the S-pindolol benzoate is S-pindolol monobenzoate. Accordingly, the salt may be of formula $[C_{14}H_{21}N_2O_2]^+[C_6H_6COO]^-$.

The pharmaceutically acceptable acid addition salt is typically crystalline. As stated herein, values of °2θ are as measured using an x-ray wavelength of CuK $α_1$ radiation (λ=1.54060 Å). If an x-ray powder diffraction pattern comprises a peak, the relative intensity of that peak is typically at least 5% or at least 10%. Error margins for the values of °2θ are typically ±0.2°2θ, but the error margin may alternatively be ±0.1°2θ.

The S-pindolol benzoate may be in the form of the crystalline polymorph of S-pindolol benzoate designated as Pattern 1. Pattern 1 of S-pindolol benzoate typically has an x-ray powder diffraction (XRPD) pattern comprising peaks at 8.1°, 11.4° and 17.0°±0.2°2θ.

The XRPD pattern of S-pindolol benzoate Pattern 1 typically further comprises peaks at 5.7°, 12.5° and 18.4°±0.2°2θ.

The XRPD pattern of S-pindolol benzoate Pattern 1 may comprise five or more peaks selected from 5.7°, 8.1°, 11.4°, 12.5°, 12.8°, 15.4°, 16.2°, 17.0°, 18.4°, 20.2°, 23.0°, 23.8°, 24.0° and 25.1°±0.2°2θ. The XRPD pattern may comprise all of these peaks. The XRPD pattern of S-pindolol benzoate Pattern 1 may comprise the following peaks.

| S-pindolol benzoate Pattern 1 | |
| --- | --- |
| Pos. [°2θ] | Rel. Int. [%] |
| 5.7 | 29.9 |
| 8.1 | 44.0 |
| 11.4 | 36.4 |
| 12.5 | 23.0 |
| 12.8 | 15.5 |
| 15.4 | 10.2 |
| 16.2 | 17.1 |
| 17.0 | 100.0 |
| 17.2 | 9.5 |
| 18.4 | 25.6 |
| 20.2 | 17.0 |
| 20.7 | 8.6 |
| 23.0 | 33.5 |
| 23.8 | 43.1 |
| 24.0 | 12.2 |
| 25.1 | 18.3 |
| 25.6 | 9.7 |
| 27.1 | 9.6 |
| 27.8 | 7.3 |
| 29.0 | 7.9 |

Figure 6:
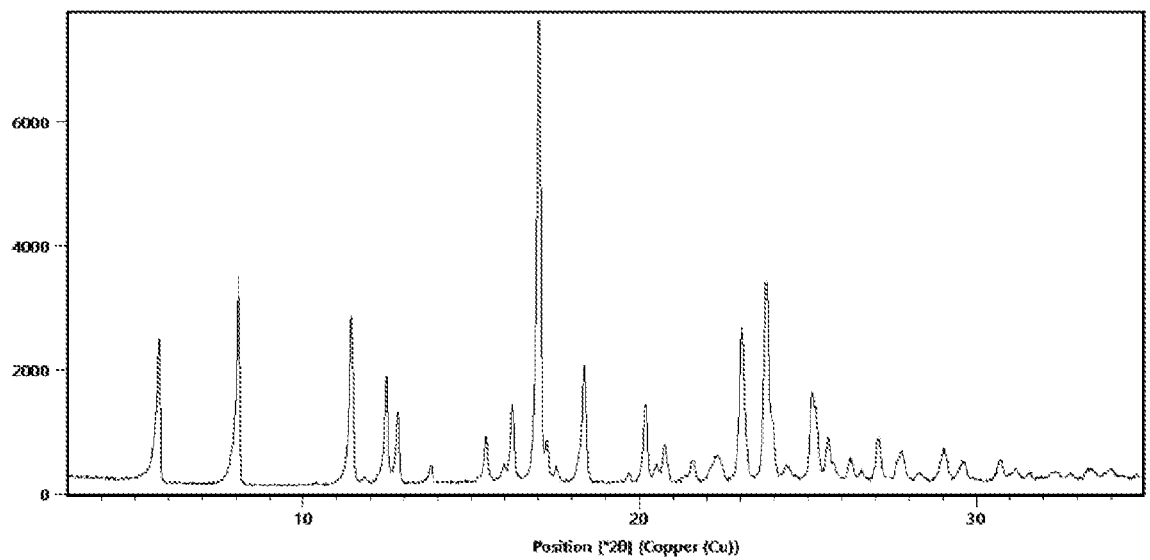
FIG. 6 shows the XRPD 2θ Diffractogram of S-pindolol benzoate Pattern 1.

The XRPD pattern of S-pindolol benzoate Pattern 1 may be substantially as shown in FIG. 6.

The infrared spectrum of S-pindolol benzoate Pattern 1 typically comprises one or more peaks in the following ranges: 1638-1648 $cm^{-1}$, 2964-2974 $cm^{-1}$, 3022-3032 $cm^{-1}$ and 3250-3260 $cm^{-1}$. For instance, the infrared spectrum may comprise peaks at about 1643 $cm^{-1}$, 2969 $cm^{-1}$, 3027 $cm^{-1}$ and 3255 $cm^{-1}$.

The melting point of S-pindolol benzoate Pattern 1 is typically in the range of 130 to 140° C., for instance about 135° C.

S-pindolol benzoate Pattern 1 may be produced by a process comprising recrystallizing S-pindolol benzoate from a solvent which is 1-butanol, 1-propanol, 1,2-dichloroethane, 1,4-dioxane, 2-methyl THF, 2-methyl-1-propanol, 2-propanol, acetone, acetonitrile, ethyl acetate, isopropyl acetate, methanol, methylisobutyl ketone and 2-ethoxyethanol.

The S-pindolol benzoate may be in the form of the crystalline polymorph of S-pindolol benzoate designated as Pattern 2. S-pindolol benzoate Pattern 2 typically has an x-ray powder diffraction (XRPD) pattern comprising a peak at 9.2°±0.2°2θ.

S-pindolol benzoate Pattern 2 typically has an x-ray powder diffraction (XRPD) pattern comprising peaks at 16.9°, 18.9° and 20.1°±0.2°2θ. The XRPD pattern of S-pindolol benzoate Pattern 2 typically further comprises peaks at 9.2°, 13.9° and 20.7°±0.2°2θ.

The XRPD pattern of S-pindolol benzoate Pattern 2 may comprise five or more peaks at selected from 8.3°, 9.2°, 12.4°, 13.0°, 13.9°, 16.9°, 18.5°, 18.9°, 19.1°, 20.1°, 20.7°, 21.3°, 23.4°, 24.8°, 26.3°, 29.4°±0.2°2θ. The XRPD pattern may comprise all of these peaks. The XRPD pattern of S-pindolol benzoate Pattern 2 may comprise the following peaks.

| S-pindolol benzoate Pattern 2 | |
| --- | --- |
| Pos. [°2θ] | Rel. Int. [%] |
| 8.3 | 14.2 |
| 9.2 | 43.4 |
| 12.4 | 27.2 |
| 13.0 | 13.9 |
| 13.9 | 34.9 |
| 16.9 | 100.0 |
| 17.8 | 7.3 |
| 18.5 | 10.4 |
| 18.9 | 47.4 |
| 19.1 | 13.3 |
| 20.1 | 55.0 |
| 20.7 | 45.0 |
| 21.3 | 44.8 |
| 23.4 | 16.9 |
| 24.8 | 39.2 |
| 25.8 | 9.9 |
| 26.3 | 13.4 |
| 26.9 | 6.4 |
| 27.9 | 6.3 |
| 29.4 | 13.7 |

Figure 11:
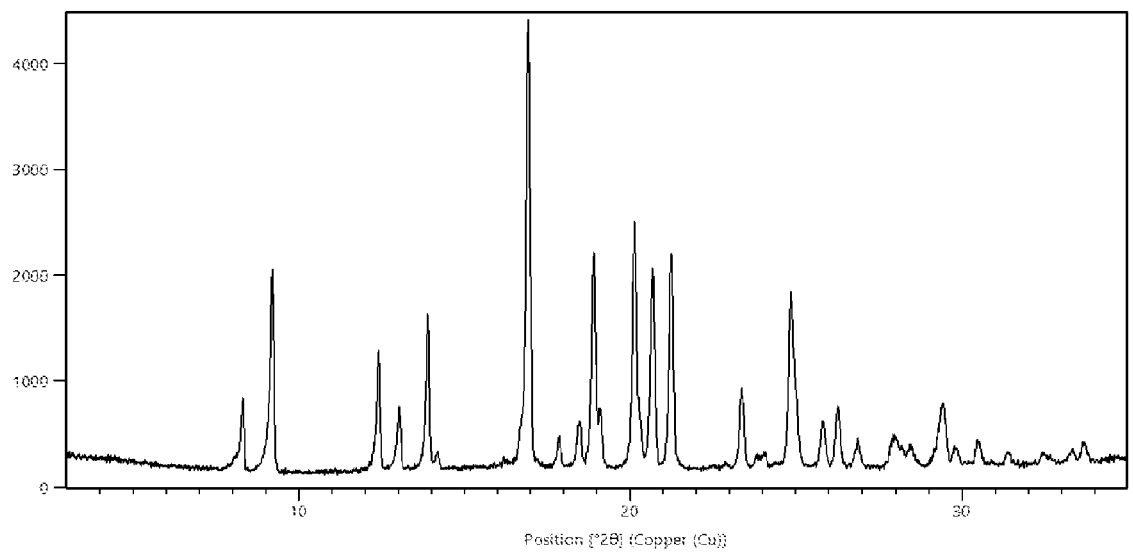
FIG. 11 shows the XRPD 2θ diffractogram of S-pindolol benzoate Pattern 2.
Figure 21:
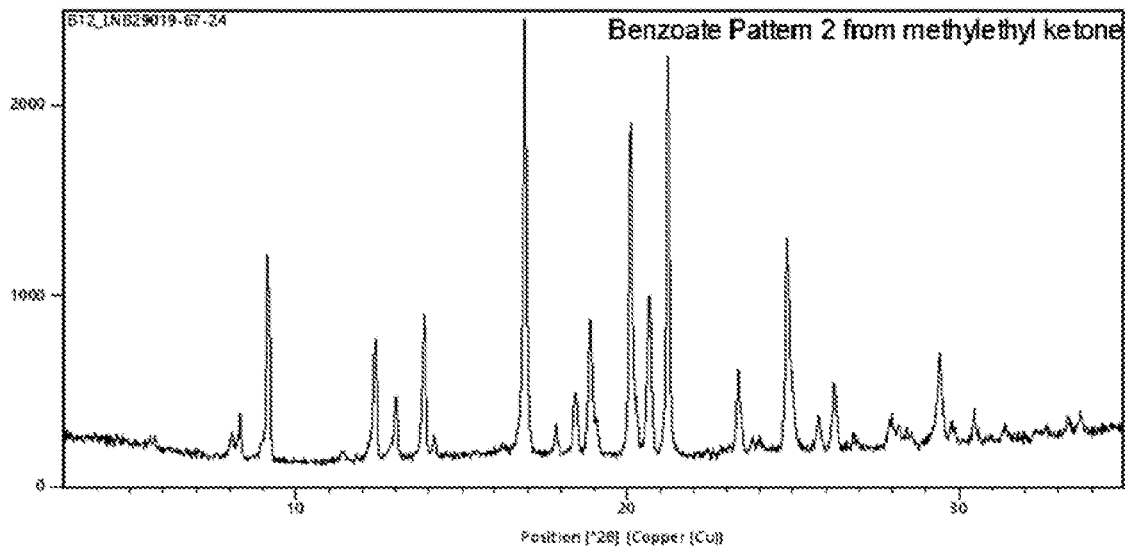
FIG. 21 shows the XRPD diffractogram of S-pindolol benzoate Pattern 2 obtained from methlylethyl ketone.

The XRPD pattern of S-pindolol benzoate Pattern 2 may be substantially as shown in FIG. 11 or FIG. 21.

The infrared spectrum of S-pindolol benzoate Pattern 2 typically comprises one or more peaks in the following ranges: 1630-1640 $cm^{-1}$, 2924-2934 $cm^{-1}$, 3093-3103 $cm^{-1}$ and 3214-3224 $cm^{-1}$. For instance the infrared spectrum may comprise peaks at about 1635 $cm^{-1}$, 2929 $cm^{-1}$, 3098 $cm^{-1}$ and 3219 $cm^{-1}$.

The melting point of S-pindolol benzoate Pattern 2 is typically in the range of 153 to 163° C., for instance about 158° C.

S-pindolol benzoate Pattern 2 may be produced by a process comprising recrystallizing S-pindolol benzoate from a solvent which is ethanol, methanol:water (for instance 95:5% v/v), methylethyl ketone, tetrahydrofuran and water. For instance, S-pindolol benzoate Pattern 2 may be obtained by recrystallizing S-pindolol benzoate from methylethyl ketone.

S-pindolol benzoate Pattern 2 has been found to be the thermodynamically stable form of S-pindolol benzoate. The S-pindolol benzoate is accordingly preferably in the form of S-pindolol benzoate Pattern 2.

The pharmaceutically acceptable acid addition salt may be S-pindolol succinate. The salt may accordingly comprise the cation derived from S-pindolol and a succinate anion. The stoichiometry of the cation and anion is typically about 1:1 or about 2:1, for instance from 0.9:1.0 to 1.1:1.0 or from 1.9:1.0 to 2.1:1.0. The S-pindolol succinate may accordingly be S-pindolol hem isuccinate or S-pindolol monosuccinate. Preferably the S-pindolol succinate is S-pindolol monosuccinate. Accordingly, the salt may be of formula $[C_{14}H_{21}N_2O_2]^+[HOOC(C_2H_4)COO]^-$ or $([C_{14}H_{21}N_2O_2]^+)_2[OOC(C_2H_4)COO]^{2-}$.

The S-pindolol succinate may be in the form of the crystalline polymorph of 5-pindolol succinate designated as Pattern 1. S-pindolol succinate Pattern 1 typically has an x-ray powder diffraction (XRPD) pattern comprising peaks at 13.3°, 16.7° and 19.5°±0.2°2θ.

The XRPD pattern of S-pindolol succinate Pattern 1 typically further comprises peaks at 8.3°, 12.2° and 12.8°±0.2°2θ. The error margin in the peak locations may be ±0.1°2θ.

The XRPD pattern of S-pindolol succinate Pattern 1 may comprise five or more peaks at selected from 8.3°, 12.2°, 12.8°, 13.3°, 16.7°, 16.9°, 19.5°, 21.5°, 22.0°, 22.7°, 24.1°, 24.3°, 25.0°±0.2°2θ. The XRPD pattern of S-pindolol succinate Pattern 1 may comprise the following peaks.

| S-pindolol succinate Pattern 1 | |
|---|---|
| Pos. [°2θ] | Rel. Int. [%] |
| 6.1 | 8.0 |
| 8.3 | 17.5 |
| 12.2 | 18.0 |
| 12.8 | 18.1 |
| 13.3 | 27.6 |
| 13.5 | 7.4 |
| 16.7 | 100.0 |
| 16.9 | 13.9 |
| 18.3 | 6.3 |
| 19.5 | 19.1 |
| 21.5 | 15.4 |
| 21.7 | 5.6 |
| 22.0 | 12.6 |
| 22.7 | 31.0 |
| 23.3 | 9.8 |
| 24.1 | 30.3 |
| 24.3 | 10.8 |
| 25.0 | 23.4 |
| 26.8 | 9.6 |
| 27.3 | 5.1 |

Figure 16:
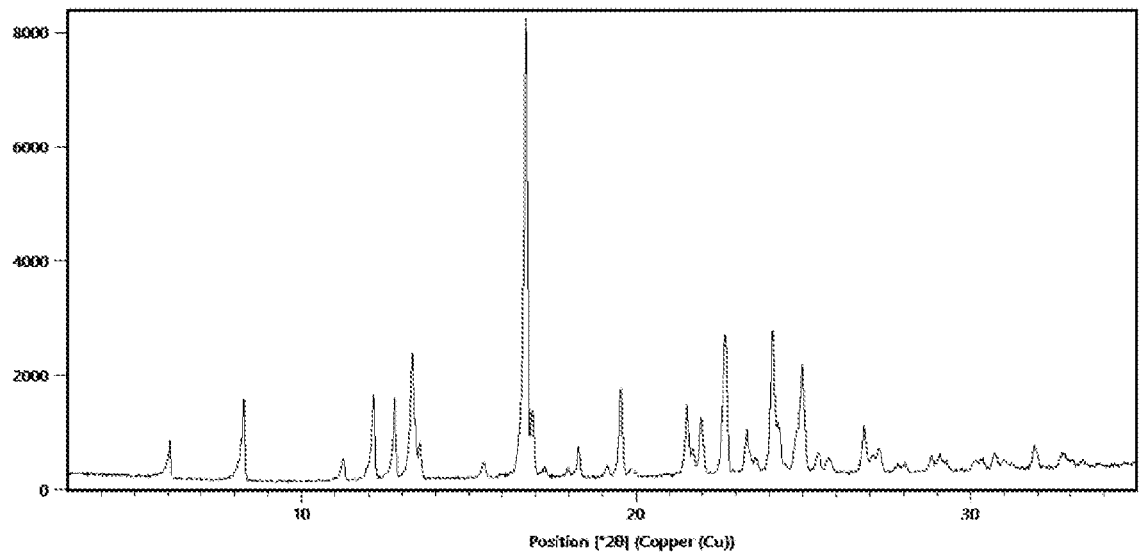
FIG. 16 shows the XRPD 2θ diffractogram of S-pindolol succinate Pattern 1.

The XRPD pattern of S-pindolol succinate Pattern 1 may be substantially as shown in FIG. 16.

The infrared spectrum of S-pindolol succinate Pattern 1 typically comprises one or more peaks in the following ranges: 1685-1695 cm$^{-1}$, 2965-2975 cm$^{-1}$, 3148-3158 cm$^{-1}$ and 3384-3394 cm$^{-1}$. For instance the infrared spectrum may comprise peaks at about 1690 cm$^{-1}$, 2970 cm$^{-1}$, 3153 cm$^{-1}$ and 3389 cm$^{-1}$.

The melting point of S-pindolol succinate Pattern 1 is typically in the range of 110 to 120° C., for instance about 115° C.

S-pindolol succinate Pattern 1 may be produced by a process comprising: (i) providing S-pindolol free base and succinic acid; (ii) adding THF to the S-pindolol free base and succinic acid to produce a mixture; (iii) cycling the temperature of the mixture from a lower of 15° C. to 30° C. to a higher temperature of 35° C. to 50° C. and back again over cycles lasting from 3 to 5 hours for a total time of from 60 to 120 hours; (iv) filtering the salt produced; and (v) drying the salt at a temperature of from 35° C. to 50° C. for from 18 to 48 hours.

The pharmaceutically acceptable acid addition salt typically has a purity of greater than or equal to about 90%, greater than or equal to about 95% or greater than or equal to about 97%. The percentage purity may be calculated as area % based on HPLC separation.

Composition

The composition of the invention comprises at least 60 wt % of the pharmaceutically acceptable acid addition salt. The composition may comprise at least 80 wt % or at least 95 wt % of the pharmaceutically acceptable acid addition salt relative to the total weight of the composition. The composition may consist essentially of the pharmaceutically acceptable acid addition salt. The composition may consist of the pharmaceutically acceptable acid addition salt.

The composition accordingly typically comprises no more than 30 wt % of R-pindolol or a salt thereof relative to the total weight of the composition. For instance, the composition may comprise no more than 10 wt %, or no more than 1 wt %, of R-pindolol or a salt thereof relative to the total weight of the composition.

The pharmaceutical composition of the invention comprises (i) the pharmaceutically acceptable acid addition salt and (ii) a pharmaceutically acceptable excipient, carrier or diluent. The pharmaceutical composition may, for instance, be: a tablet, capsule, powder, solution or suspension for oral administration; a solution or suspension for injection; or a solution, suspension or powder for inhalation. The pharmaceutical composition is typically a tablet.

Pharmaceutically acceptable excipients, carriers and diluents are well known to the skilled person.

The diluent may be any pharmaceutically acceptable diluent. The diluent is typically suitable for parenteral administration or for oral administration. Examples of suitable liquid diluents include water, ethanol and glycerol. The diluent may alternatively be selected from solid diluents such as lactose, dextrose, saccharose, cellulose, corn starch and potato starch. The diluent may contain buffer components to control the pH. The buffers may be derived from phosphate, citrate or acetate. The diluent may also contain sodium chloride.

The pharmaceutical composition may comprise an excipient selected from:

lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tableting, sugar coating, or film coating processes.

The pharmaceutical composition may for instance be a tablet comprising one or more excipients selected from magnesium stearate, colloidal silica, microcrystalline cellulose, strearyl fumarate and starch.

Compositions which are liquid dispersions for oral administration may be syrups, emulsions and suspensions. The syrups may contain as carriers, for example, saccharose, glycerine, mannitol or sorbitol.

Compositions which are suspensions or emulsions may contain as carrier, for example a natural gum, agar, sodium alginate, pectin, methylcellulose, carboxymethylcellulose, or polyvinyl alcohol. The suspension or solutions for intramuscular injections may contain, together with the pharmaceutically acceptable acid addition sat, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion, or for inhalation, may contain as carrier, for example, sterile water or they may be in the form of sterile, aqueous, isotonic saline solutions.

The pharmaceutical composition may comprise the pharmaceutically acceptable acid addition salt in an amount equivalent to from 0.1 to 1000 mg of S-pindolol free base. For instance, the pharmaceutical composition may comprise the pharmaceutically acceptable acid addition salt in an amount equivalent to from 80 to 160 mg or from 2.5 to 50 mg of S-pindolol free base. The pharmaceutical composition may comprise the salt in an amount equivalent to from 2.5 to 15 mg of S-pindolol free base. For example, 3.7 mg of S-pindolol benzoate (molecular weight 370.4 gmol$^{-1}$) is equivalent to 2.5 mg S-pindolol free base (molecular weight 248.3 gmol$^{-1}$).

The pharmaceutical composition is typically substantially free of R-pindolol or a salt thereof. For instance, the pharmaceutical composition may comprise less than 1.0 wt %, or less than 0.5 wt %, of R-pindolol or a salt thereof.

Medical Uses

The pharmaceutically acceptable acid addition salt is useful in the treatment or prevention of a disease or condition selected from cachexia, sarcopenia, a neuromuscular disorder, muscle weakness, hypertension, heart failure, atrial fibrillation, heart attack, angina pectoris, glaucoma and anxiety. Typically the disease or condition is selected from cachexia and muscle weakness.

The cachexia may be caused by an underlying condition. For instance, the cachexia may be caused by cancer, heart failure, chronic obstructive pulmonary diseases (COPD), liver failure, kidney failure, stroke, rheumatoid arthritis, severe burn injury or HIV/AIDS. The muscle weakness may be caused by an underlying condition. For instance, the muscle weakness may be caused by trauma, musculoskeletal injury, surgery or immobilization. The muscle weakness may be intensive care unit acquired weakness (ICUAW). The neuromuscular disorder may for instance be amyotrophic lateral sclerosis.

The invention also provides a method of treating or preventing a disease or condition selected from cachexia, sarcopenia, a neuromuscular disorder, muscle weakness, hypertension, heart failure, atrial fibrillation, heart attack, angina pectoris, glaucoma and anxiety in an individual, the method comprising administering a therapeutically effective amount of the pharmaceutically acceptable acid addition salt to the individual.

The pharmaceutically acceptable acid addition salt is typically administered orally or parenterally.

An effective amount of the pharmaceutically acceptable acid addition salt is typically an amount equivalent to from 0.1 to 1000 mg of S-pindolol free base for a single dose. For instance, a single dose of the pharmaceutically acceptable acid addition salt may be a dose equivalent to from 2.5 to 50 mg or from 80 to 160 mg of S-pindolol free base. A single dose may be an amount of the salt equivalent to from 2.5 to 15 mg of S-pindolol free base. The dose may be administered once, twice or three times a day.

The following Examples illustrate the invention.

EXAMPLES

Example 1

Salts of S-Pindolol

Methods of Analysis

X-Ray Powder Diffraction (XRPD)

XRPD analysis was carried out on a PANalytical X'pert pro with PIXcel detector (128 channels), scanning the samples between 3 and 35°2θ. The material was gently ground to release any agglomerates and loaded onto a multi-well plate with Mylar polymer film to support the sample. The multi-well plate was then placed into the diffractometer and analysed using Cu K radiation ($\alpha_1$ λ=1.54060 Å; $\alpha_2$=1.54443 Å; β=1.39225 Å; $\alpha_1$: $\alpha_2$ ratio=0.5) running in transmission mode (step size 0.0130°2θ, step time 18.87s) using 40 kV/40 mA generator settings. Data were visualized and images generated using the HighScore Plus 4.7 desktop application (PANalytical, 2017).

Thermogravimetric/Differential Scanning Calorimetry (TG/DSC)

Approximately, 5-10 mg of material was added into a pre-tared open aluminium pan and loaded into a TA Instruments Discovery SDT 650 Auto-Simultaneous DSC and held at room temperature. The sample was then heated at a rate of 10° C./min from 30° C. to 400° C. during which time the change in sample weight was recorded along with the heat flow response (DSC). Nitrogen was used as the purge gas, at a flow rate of 300 cm$^3$/min.

Differential Scanning Calorimetry (DSC)

Approximately 5 mg of material was weighed into an aluminium DSC pan and sealed non-hermetically with an aluminium lid. The sample pan was then loaded into a TA Instruments Discovery DSC 2500 (equipped with a RC90 cooler) cooled and held at 20° C. Once a stable heat-flow response was obtained, the sample and reference were heated to 180° C. at scan rate of 10° C./min and the resulting heat flow response monitored. Nitrogen was used as the purge gas, at a flow rate of 50 cm$^3$/min.

Infrared Spectroscopy (IR)

Infrared spectroscopy was carried out on a Bruker ALPHA P spectrometer. Sufficient material was placed onto the centre of the plate of the spectrometer and the spectra were obtained using the following parameters:

Resolution: 4 cm$^{-1}$
Background Scan Time: 16 scans
Sample Scan Time: 16 scans
Data Collection: 4000 to 400 cm$^{-1}$
Result Spectrum: Transmittance
Software: OPUS version 6

Nuclear Magnetic Resonance (NMR)

NMR experiments were performed on a Bruker AVIIIHD spectrometer equipped with a DCH cryoprobe operating at 500.12 MHz for protons. Experiments were performed in deuterated DMSO or methanol and each sample was prepared to ca. 10 mM concentration.

Dynamic Vapour Sorption (DVS)

Approximately 10-20 mg of sample was placed into a mesh vapour sorption balance pan and loaded into an Intrinsic dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Variable Temperature X-Ray Powder Diffraction (VT-XRPD)

VT-XRPD analysis was carried out on a Philips X'Pert Pro Multipurpose diffractometer equipped with a temperature chamber. The samples were scanned between 4 and 35.99 °2θ using Cu K radiation ($\alpha_1\lambda=1.54060$ Å; $\alpha_2=1.54443$ Å; $\beta=1.39225$ Å; $\alpha_1:\alpha_2$ ratio=0.5) running in Bragg-Brentano geometry (step size 0.008 °2θ) using 40 kV/40 mA generator settings. Experimental parameters were performed as follows: Scan at 30° C.; Heat to 75° C. at 10° C./min; Hold for 5 minutes; Scan at 75° C.; Heat to 87° C. at 2° C./min; Hold for 5 minutes; Scan at 87° C.; Heat to 105° C. at 2° C./min; Hold for 5 minutes; Scan at 105° C.; Heat to 115° C. at 2° C./min; Hold for 5 minutes; Scan at 115° C.; Cool to 30° C. at 10° C./min; Scan at 30° C.

High Performance Liquid Chromatography-Ultraviolet Detection (HPLC-UV)

Instrument: Dionex Ultimate 3000
Column: Agilent Zorbax, SB-C18, 150 mm×4.6 mm, 3.5 μm
Column Temperature: 25° C.
Autosampler Temperature: Ambient
UV wavelength: 254 nm
Injection Volume: 3 μl
Flow Rate: 1.0 ml/min
Mobile Phase A: 1.36 g Potassium dihydrogen phosphate+1000 mL water. Adjust pH with phosphoric acid to 4.0±0.05. Filter through a 0.45 μm membrane and degas
Mobile Phase B: Acetonitrile: Methanol (95:5 v/v)
Diluent: Water: Acetonitrile (20:80 v/v)
Gradient program:

| Time (minutes) | Solvent B [%] |
|---|---|
| 0 | 5 |
| 5 | 5 |
| 15 | 70 |
| 25 | 70 |
| 30 | 5 |
| 35 | 5 |

Characterisation of S-Pindolol Free Base

A sample of S-pindolol free base was characterised. XRPD analysis showed S-pindolol free base was highly crystalline. The XRPD pattern of S-pindolol free base (free base Pattern 1) is shown in FIG. 1.

TG/DSC analysis found no mass losses by TG until degradation from ca. 200° C.

This indicated that the material was anhydrous and non-solvated. An endothermic event was observed in the DSC with an onset of 82° C. and peak of 84° C. which was attributed to a solid-solid transition. A larger endothermic event was observed with an onset of 93° C. and peak of 95° C. due to melting.

DVS analysis determined the material was slightly hygroscopic with a mass uptake of 0.36 wt. % (0.05 eq. of water) at 90% RH. XRPD analysis post-DVS showed the material remained unchanged.

Primary Salt Investigations 72 samples of 40 mg of ACM-001 free base were weighed into 2 mL vials. 0.5 mL of the appropriate solvent was added to each vial, followed by 1.1 eq. of the appropriate counterion.

The counterions used were those derived from the following acids: hydrochloric acid ($pKa_1$ of −6), sulfuric acid ($pKa_1$ of −3), p-toluenesulfonic acid.H$_2$O ($pKa_1$ of −1.34), methanesulfonic acid ($pKa_1$ of −1.2), maleic acid ($pKa_1$ of 1.92), phosphoric acid ($pKa_1$ of 1.96), L-tartaric acid ($pKa_1$ of 3.02), fumaric acid ($pKa_1$ of 3.03), citric acid ($pKa_1$ of 3.13), S-(+)-mandelic acid ($pKa_1$ of 3.37), benzoic acid ($pKa_1$ of 4.19) and succinic acid ($pKa_1$ of 4.21).

The solvents used were water, ethanol, 2-propanol, ethyl acetate, acetone and tetrahydrofuran (THF).

The samples were temperature cycled between ambient temperature and 40° C. in 4 hour cycles for 72 hours. Any solids formed were isolated via centrifugation before being analysed by XRPD.

A number of the solids obtained after initial temperature cycling were found to be coloured. In particular, the products formed using sulfuric acid, p-toluenesulfonic acid, methanesulfonic acid, maleic acid, phosphoric acid, L-tartaric acid, fumaric acid and citric acid were coloured when certain solvents were used.

0.5 mL of anti-solvent was then added to vials that contained insufficient solids for XRPD analysis (acetone was used for the experiments in water and heptane was used for all other samples). These samples were then temperature cycled as before for a further 24 hours. Additional solids produced at this stage were isolated via centrifugation and analysed by XRPD. Samples without solids were placed in a fridge (2-8° C.) for 72 hours. No solids were yielded so the samples were uncapped and left to evaporate for up to a week. Any solids and gels obtained were analysed by XRPD.

Samples which remained in solution after 7 days as well as all samples obtained by temperature cycling, anti-solvent addition and evaporation at ambient were placed in an oven at 40° C. for 72 hours to dry and then analysed by XRPD. Table 1 shows the observations made after drying, where "s" indicates formation of a solid, "gm" indicates formation of a gum and "cryst" indicates formation of large crystals.

TABLE 1

Observations after drying

| | Hydrochloric acid | Sulfuric acid | p-Toluene-sulfonic acid | Methane-sulfonic acid | Maleic acid | Phosphoric acid | l-Tartaric acid | Fumaric acid | Citric acid | l-Mandelic acid | Benzoic acid | Succinic acid |
|---|---|---|---|---|---|---|---|---|---|---|---|---|
| Water | s | glass | gm | gm | gm | gm | gm | gm | gm | gm | cryst | gm |
| Ethanol | s | gm | gm | gm | gm | gm | gm | s | gm | gm | gm | s |
| 2-Propanol | s | gm | gm | gm | gm | gm | gm | s | gm | gm | s | s |

TABLE 1-continued

Observations after drying

| | Hydrochloric acid | Sulfuric acid | p-Toluene-sulfonic acid | Methane-sulfonic acid | Maleic acid | Phosphoric acid | l-Tartaric acid | Fumaric acid | Citric acid | l-Mandelic acid | Benzoic acid | Succinic acid |
|---|---|---|---|---|---|---|---|---|---|---|---|---|
| Ethyl acetate | s | gm | gm | gm | gm | gm | s | s | gm | gm | s | s |
| Acetone | s | gm | gm | gm | gm | gm | gm | s | gm | gm | s | s |
| THF | s | gm | gm | gm | gm | gm | gm | s | gm | gm | s | s |

The products obtained using sulfuric acid, p-toluenesulfonic acid, methanesulfonic acid, maleic acid, phosphoric acid, L-tartaric acid, citric acid and L-mandelic acid were mostly found to be amorphous. Many of these products were also strongly coloured.

The XRPD of the product formed using hydrochloric acid was found to correspond to that of S-pindolol free base.

Gums were formed from most solvents when S-pindolol was treated with tartaric acid. A solid product was formed when ethyl acetate was used as the solvent. However, following XRPD analysis the solid product from ethyl acetate and tartaric acid was found to be S-pindolol free base. It was not therefore possible to produce a crystalline salt of S-pindolol with tartaric acid.

The salts formed with fumaric acid, benzoic acid and succinic acid were found to be crystalline, with XRPD patterns different from that of S-pindolol free base. The fumaric acid salts were coloured when formed from water, ethanol, 2-propanol and acetone, and white when formed from ethyl acetate and THF. The succinic acid salts were coloured when formed from water, and were otherwise white. The benzoic acid salts were white when formed from any solvent.

The primary salt screen therefore found that crystalline solid salt forms could be formed from fumaric acid, benzoic acid and succinic acid. Salts formed with these three acids were characterised further.

Characterisation of Fumarate Salt

Figure 2:
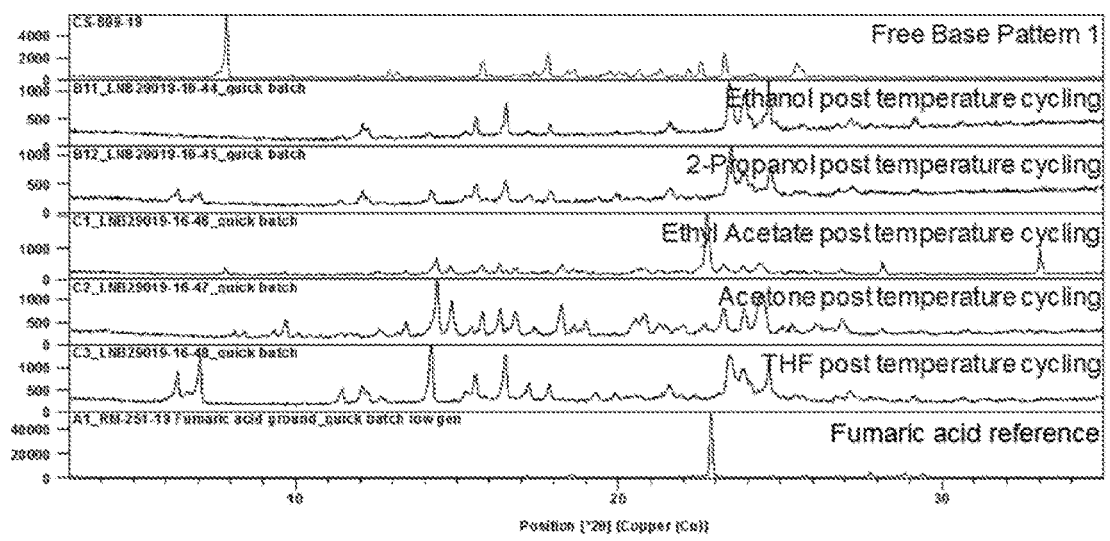
FIG. 2 shows the XRPD 2θ diffractograms of the solids obtained from treatment of S-pindolol with fumaric acid.

The solids recovered from the fumaric acid experiments in ethanol, 2-propanol, acetone and THF were crystalline and not consistent with free base Pattern 1, as shown in FIG. 2. Fumarate Pattern 1 was obtained from ethanol, Pattern 2 from 2-propanol and THF, and Pattern 3 from acetone.

Pattern 1 and 2 are similar, although peaks below 10°2θ were not present in Pattern 1. Therefore, Pattern 2 may be a mixture containing Pattern 1.

Patterns 1, 2 and 3 were characterised as follows.

Hemi-Fumarate Pattern 1

Figure 3:
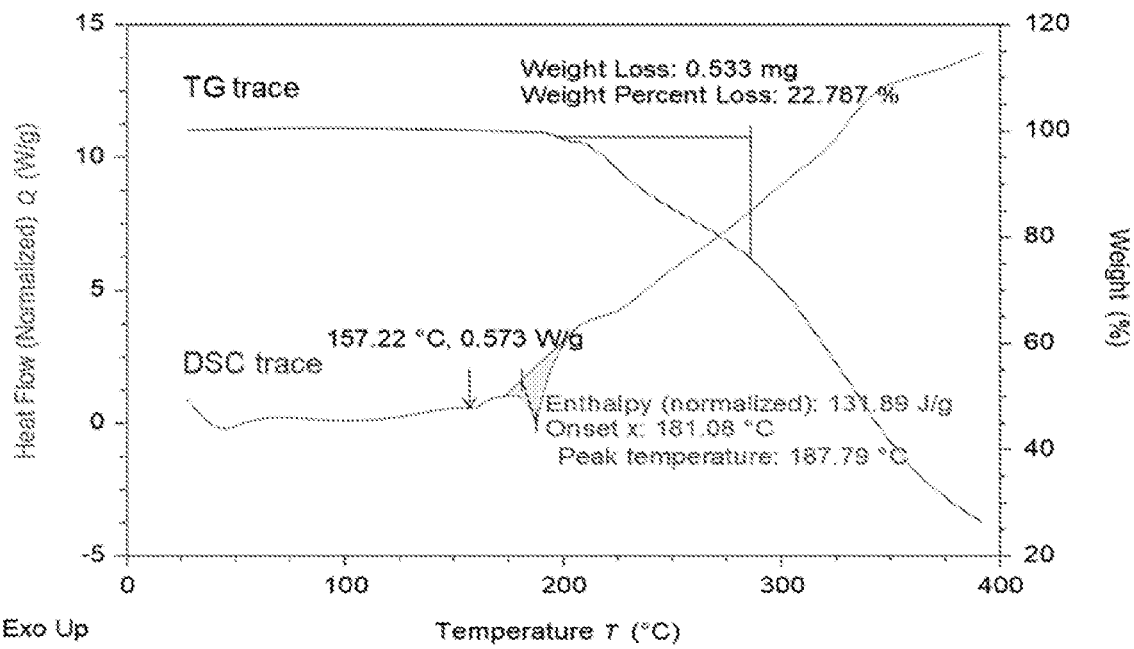
FIG. 3 shows the TG/DSC thermogram of S-pindolol hemi-fumarate Pattern 1.

During TG analysis, a 22.8% weight loss (0.40 eq. fumaric acid) was observed between 200° C. and 280° C., this could be due to degradation. Decomposition occurred above 200° C. An endothermic event associated with melting was observed in the DSC trace with an onset at 181° C. and peak at 188° C. A small endothermic event was noted at 157° C., higher than the two other hemi-fumarate forms. The TG and DSC traces are shown in FIG. 3.

Half an equivalent of fumaric acid was noted in the $^1$H NMR spectrum in DMSO-$d_6$. No ethanol was present. Peak shifting compared to the S-pindolol free base and a broad water peak were observed, indicating salt formation has occurred.

Hemi-Fumarate Pattern 2

Figure 4:
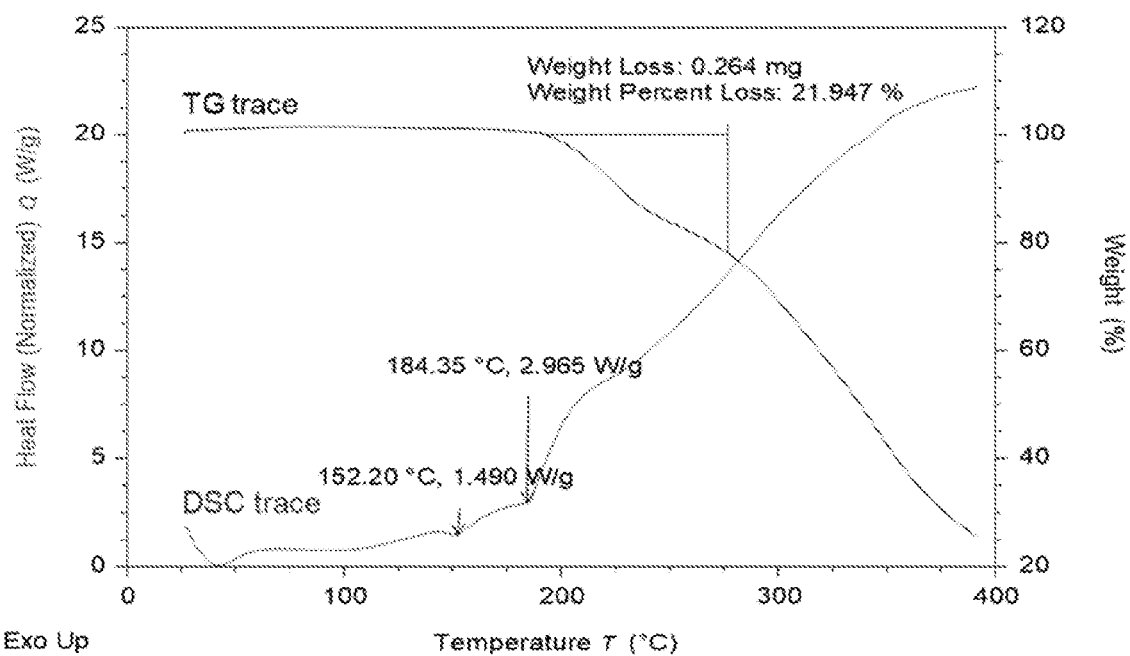
FIG. 4 shows the TG/DSC thermogram of S-pindolol hemi-fumarate Pattern 2.

During TG analysis, a 21.9% weight loss (potentially 0.39 eq. fumaric acid) was observed between 180° C. and 280° C., this could be due to degradation. Decomposition occurred above 200° C. Two shallow endothermic events were observed in the DSC trace with peaks at 152° C. and 184° C. The second event was associated with the onset of decomposition. The TG and DSC traces are shown in FIG. 4.

$^1$H NMR in DMSO-$d_6$ determined there was approximately 0.5 equivalents of fumaric acid in the sample. 1.08 wt. % (0.04 eq.) of THF was present. Peak shifting compared to S-pindolol free base and a broad water peak were observed, indicating salt formation has occurred.

Hemi-Fumarate Pattern 3

Figure 5:
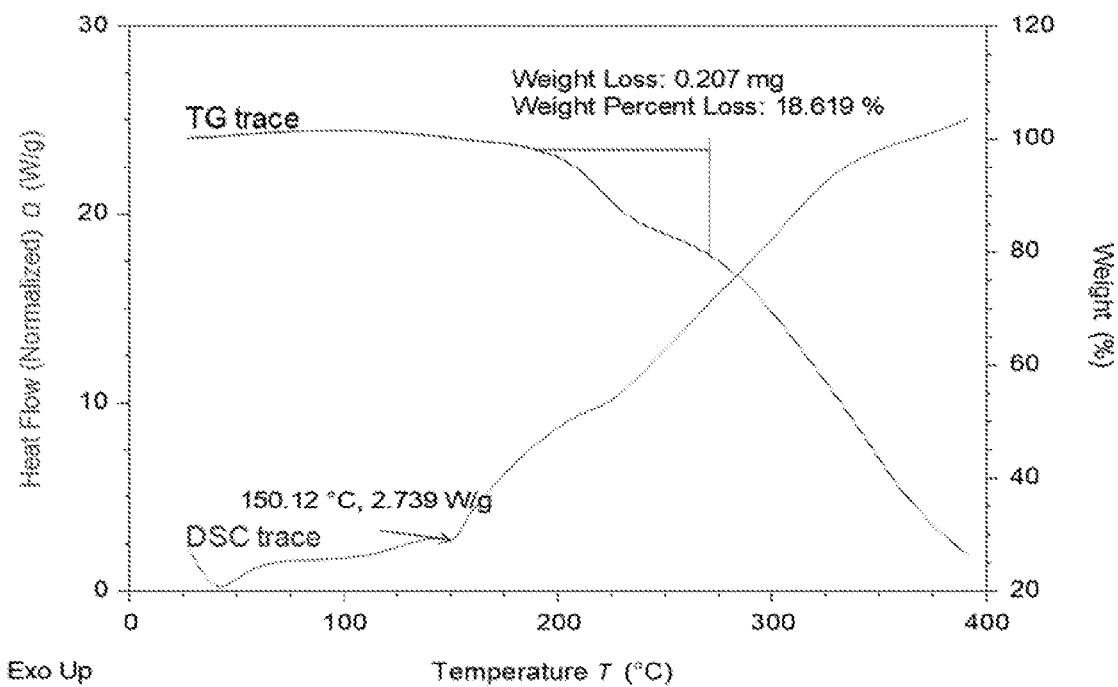
FIG. 5 shows the TG/DSC thermogram of S-pindolol hemi-fumarate Pattern 3.

In the TG trace, a 18.6% weight loss (potentially 0.34 eq. fumaric acid) was observed between 200° C. to approx. 270° C. Decomposition occurred above 200° C. One shallow endothermic event due to melting was observed in the DSC trace with a peak at 150° C. The TG and DSC traces are shown in FIG. 5.

$^1$H NMR in DMSO-$d_6$, found a broad peak corresponding to approximately 0.5 equivalents of fumaric acid at 6.35 ppm. A possible acetone peak was observed at 2.09 ppm (7.09 wt. % or 0.3 eq.). However, a peak was observed in the free base NMR spectrum in that location so there is likely some overlap. Peak shifting compared to the ACM-001 free base and a broad water peak were observed, indicating salt formation has occurred.

Stability Testing of Fumarate Salt Forms

Samples of S-pindolol hemi-fumarate Pattern 2 was stored at 60° C. (sealed vial) or 40° C./75% RH (open vial) for 7 days. The sample stored at 60° C. converted to Pattern 1. The sample stored at 40° C./75% RH converted to a different form, Pattern 4.

Preparation and Characterisation of S-Pindolol Benzoate Pattern 1

S-Pindolol Benzoate Pattern 1 Preparation 271.69 mg (1.1 eq.) of benzoic acid was added to ca. 500 mg of S-pindolol free base in a scintillation vial. The sample vial which contained the acid was rinsed with 1 mL of ethyl acetate and the washing was added to the scintillation vial. A further 1 mL of ethyl acetate was added and a beige solution with a small amount of undissolved benzoic acid was noted.

The scintillation vial was capped and sealed with parafilm and then temperature cycled between ambient temperature and 40° C. over 4-hour cycles for ca. 72 hours.

After 72 hours, a sub-sample was analysed by XRPD. The sample matched benzoate Pattern 1, therefore the sample was filtered on a Buchner funnel and placed in a pre-weighed sample vial. The solid was dried at 40° C. for ca. 21 hours.

The benzoate salt was characterised by XRPD, $^1$H NMR, TG/DSC, DSC, and FT-IR.

S-Pindolol Benzoate Pattern 1 Characterisation

XRPD analysis showed S-pindolol benzoate was highly crystalline. The pattern (show in FIG. 6) was designated as S-pindolol benzoate Pattern 1. The 2θ values and peak intensities for S-pindolol benzoate Pattern 1 are shown in Table 2 below.

TABLE 2

| Pos. [°2θ] | d-spacing [Å] | Height [cts] | Rel. Int. [%] |
|---|---|---|---|
| 5.7262 | 15.43427 | 2286.42 | 29.92 |
| 8.0878 | 10.93206 | 3364.48 | 44.03 |
| 11.4359 | 7.73790 | 2784.69 | 36.44 |
| 12.4821 | 7.09161 | 1758.59 | 23.02 |
| 12.8263 | 6.90206 | 1182.78 | 15.48 |
| 15.4499 | 5.73539 | 775.90 | 10.15 |
| 16.2200 | 5.46476 | 1309.70 | 17.14 |
| 17.0078 | 5.21337 | 7640.98 | 100.00 |
| 17.2496 | 5.14084 | 723.82 | 9.47 |
| 18.3698 | 4.82980 | 1952.51 | 25.55 |
| 20.1801 | 4.40042 | 1296.24 | 16.96 |
| 20.7477 | 4.28131 | 655.66 | 8.58 |
| 23.0325 | 3.86152 | 2557.41 | 33.47 |
| 23.7511 | 3.74629 | 3291.45 | 43.08 |
| 23.9697 | 3.71261 | 931.42 | 12.19 |
| 25.0959 | 3.54851 | 1400.34 | 18.33 |
| 25.6148 | 3.47778 | 743.27 | 9.73 |
| 27.1119 | 3.28905 | 730.31 | 9.56 |
| 27.7902 | 3.21030 | 555.04 | 7.26 |
| 29.0215 | 3.07683 | 601.94 | 7.88 |

The single crystal parameters of S-pindolol benzoate Pattern 1 were identified. The unit cell dimensions of the collected structure were found to be as follows:

Monoclinic P21
a=8.4937(5) Å α=90°
b=15.2956(9) Å β=98.981(2)°
c=15.5169(9) Å γ=90°
Volume=1991.2(2) Å$^3$
Z=4, Z'=2

The final refinement parameters were as follows:
$R_1$[I>2σ(I)]=2.99%
GooF (Goodness of fit)=1.058
$wR_2$ (all data)=8.28%
$R_{int}$=3.15%
Flack=−0.03(4)

By $^1$H NMR, a 1:1 ratio of benzoic acid and S-pindolol was observed and a broad water peak was present, indicating salt formation was successful. The presence of 0.69 wt. % (0.03 eq.) of ethyl acetate was observed.

Figure 7:
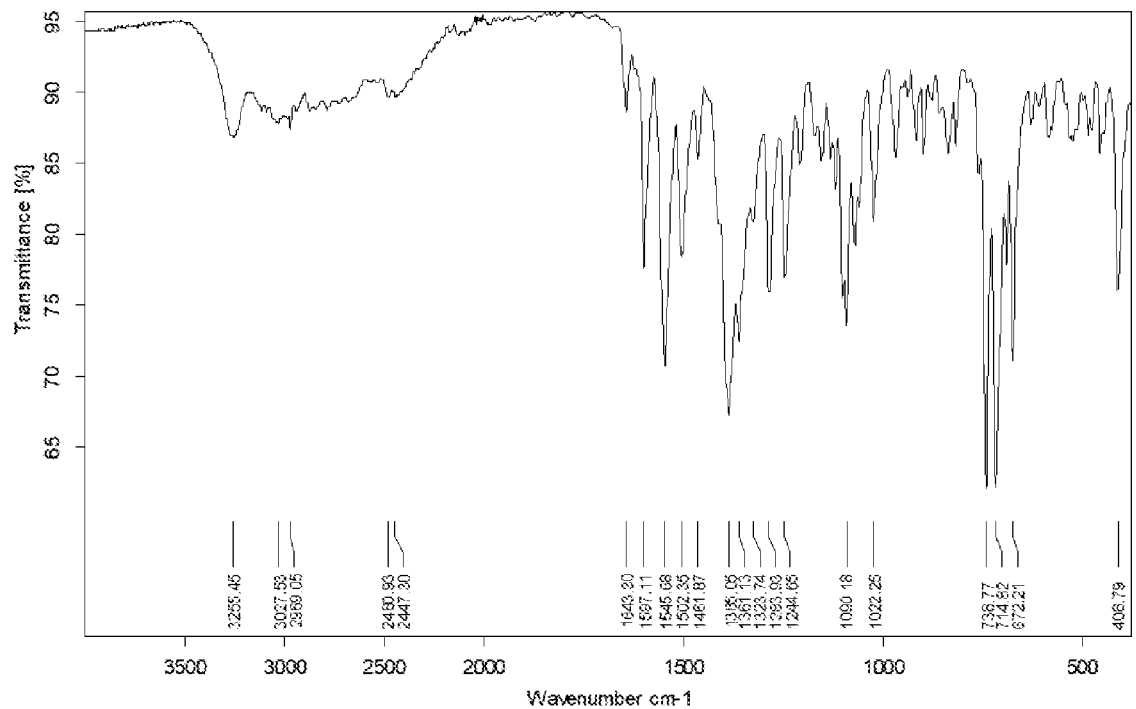
FIG. 7 shows the FT-IR spectrum of S-pindolol benzoate Pattern 1.
Figure 8:
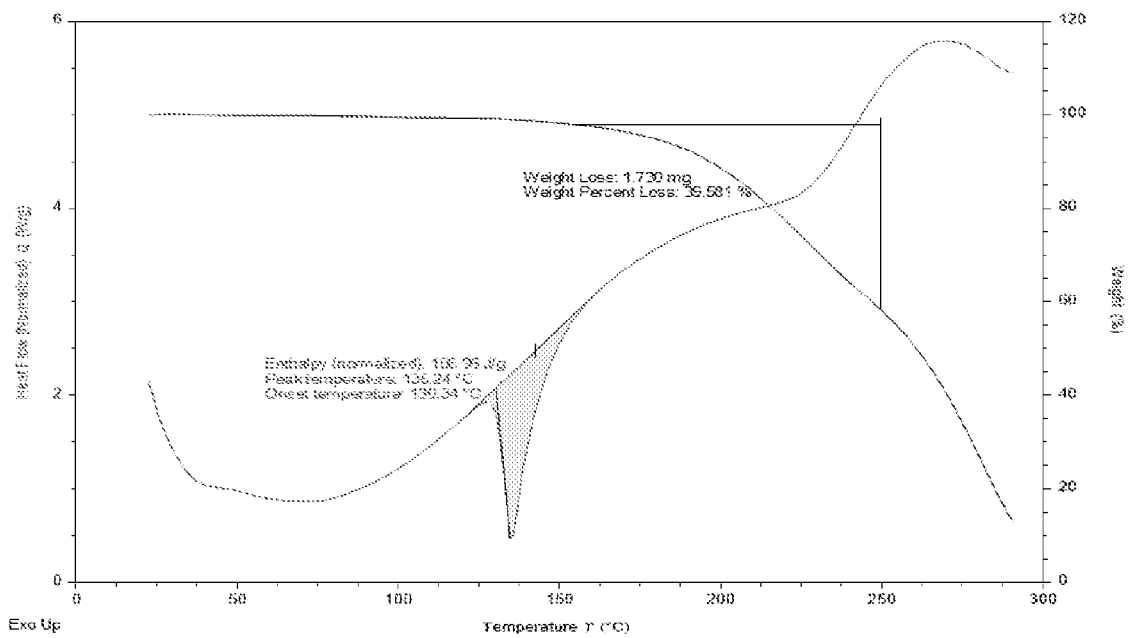
FIG. 8 shows the TG/DSC thermogram of S-pindolol benzoate Pattern 1.
Figure 9:
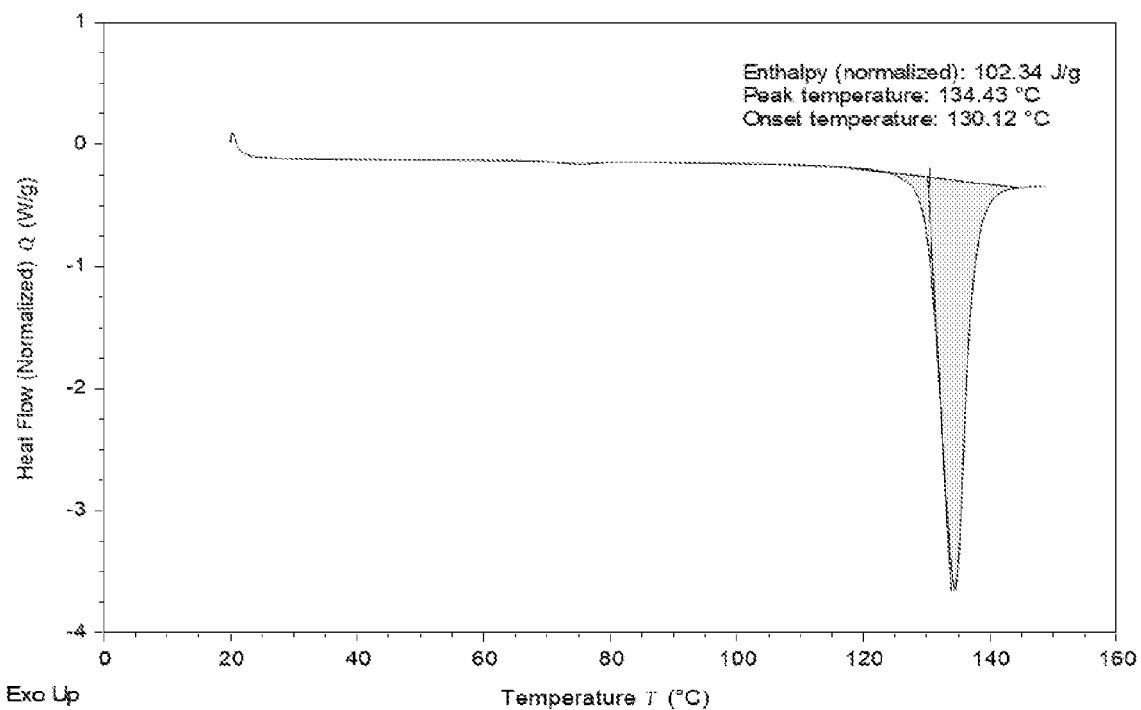
FIG. 9 shows the DSC thermogram of S-pindolol benzoate Pattern 1 (first heating cycle).
Figure 10:
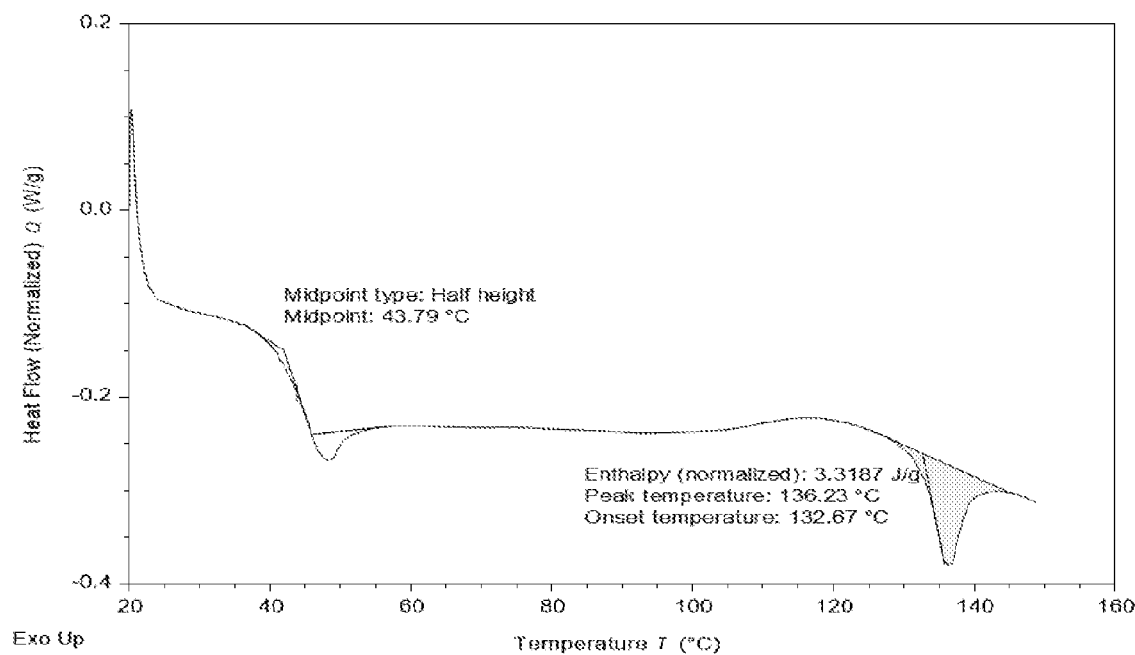
FIG. 10 shows the DSC thermogram of S-pindolol benzoate Pattern 1 (second heating cycle).

FT-IR spectrum matched the supplied structure, see FIG. 7. The following peaks were observed and assigned:
Broad O—H stretch ~3255-2447 cm$^{-1}$
N—H stretch ~3255 cm$^{-1}$
Aromatic C—H stretch ~3027 cm$^{-1}$
Aliphatic C—H stretch ~2969 cm$^{-1}$
Alkene C=C ~1643 cm$^{-1}$ TG and DSC scans of S-pindolol benzoate Pattern 1 are shown in FIGS. 8 to 10. TG/DSC analysis found a 40% mass loss by TG between 150° C. and 250° C. followed by degradation. This weight loss was likely due to degradation but also equates to 2 eq. of benzoic acid. An endothermic event was observed in the DSC with an onset of 130° C. and peak of 135° C.

DSC analysis found a sharp endothermic event with an onset at 130° C. and peak at 135° C. This corresponds to the melt and matches the TG/DSC data. No events were observed in the cooling cycle. A glass transition with a midpoint at 44° C. and an endothermic event with an onset at 133° C. and peak at 136° C. were observed in the second heating cycle.

Preparation and Characterisation of S-Pindolol Benzoate Pattern 2

S-Pindolol Benzoate Pattern 2 Preparation

Ca. 5 g of S-pindolol free base was combined with ca. 2.7 g of benzoic acid. The benzoic acid sample vial was rinsed with 2 mL of ethyl acetate. The washing and a further 16 mL of ethyl acetate were added to the combined sample to form a white slurry.

The sample was temperature cycled between ambient and 40° C. over 4-hour cycles for ca. 24 hours.

The material was filtered on a Büchner funnel and left to dry on the filter paper for ca. 5 minutes. The material was then returned to the sample vial and dried under vacuum at 40° C. for ca. 6 hours.

The benzoate salt was characterised by XRPD, $^1$H NMR, TG/DSC, DSC, and FT-IR.

S-Pindolol Benzoate Pattern 2 Characterisation

XRPD analysis showed S-pindolol benzoate was highly crystalline. The pattern (as shown in FIG. 11) was designated as S-pindolol benzoate Pattern 2. The 2θ values and peak intensities for S-pindolol benzoate Pattern 2 are shown in Table 3 below.

TABLE 3

| Pos. [°2θ] | d-spacing [Å] | Height [cts] | Rel. Int. [%] |
|---|---|---|---|
| 8.327 | 10.61854 | 609.96 | 14.15 |
| 9.219 | 9.59309 | 1869.96 | 43.39 |
| 12.409 | 7.13300 | 1171.80 | 27.19 |
| 13.042 | 6.78854 | 600.89 | 13.94 |
| 13.904 | 6.36935 | 1501.76 | 34.85 |
| 16.935 | 5.23576 | 4309.31 | 100.00 |
| 17.843 | 4.97118 | 314.50 | 7.30 |
| 18.492 | 4.79822 | 447.77 | 10.39 |
| 18.910 | 4.69300 | 2041.50 | 47.37 |
| 19.091 | 4.64903 | 572.23 | 13.28 |
| 20.130 | 4.41129 | 2368.05 | 54.95 |
| 20.680 | 4.29508 | 1938.24 | 44.98 |
| 21.268 | 4.17769 | 1929.33 | 44.77 |
| 23.381 | 3.80473 | 729.14 | 16.92 |
| 24.846 | 3.58368 | 1688.11 | 39.17 |
| 25.810 | 3.45199 | 426.04 | 9.89 |
| 26.269 | 3.39271 | 579.08 | 13.44 |
| 26.871 | 3.31803 | 275.38 | 6.39 |
| 27.911 | 3.19663 | 270.98 | 6.29 |
| 29.426 | 3.03548 | 589.78 | 13.69 |

The single crystal parameters of S-pindolol benzoate Pattern 2 were identified. The unit cell dimensions of the collected structure were found to be as follows:

Monoclinic P2$_1$
a=9.9330(2) Å α=90°
b=9.5832(2) Å β=107.2020(10)°
c=10.9875(3) Å γ=90°
Volume=999.11(4) Å$^3$
Z=2, Z'=1

The final refinement parameters were as follows:
$R_1$[I>2σ(I)]=2.58%
GooF (Goodness of fit)=1.040
$wR_2$ (all data)=6.73%
$R_{int}$=2.86%
Flack=0.01(7)

By $^1$H NMR, a 1:1 ratio of benzoic acid and S-pindolol was observed. 0.25 wt. % (0.01 eq.) of ethyl acetate was also found in the spectrum. A broad water peak and peak shifting indicated salt formation was successful.

Figure 12:
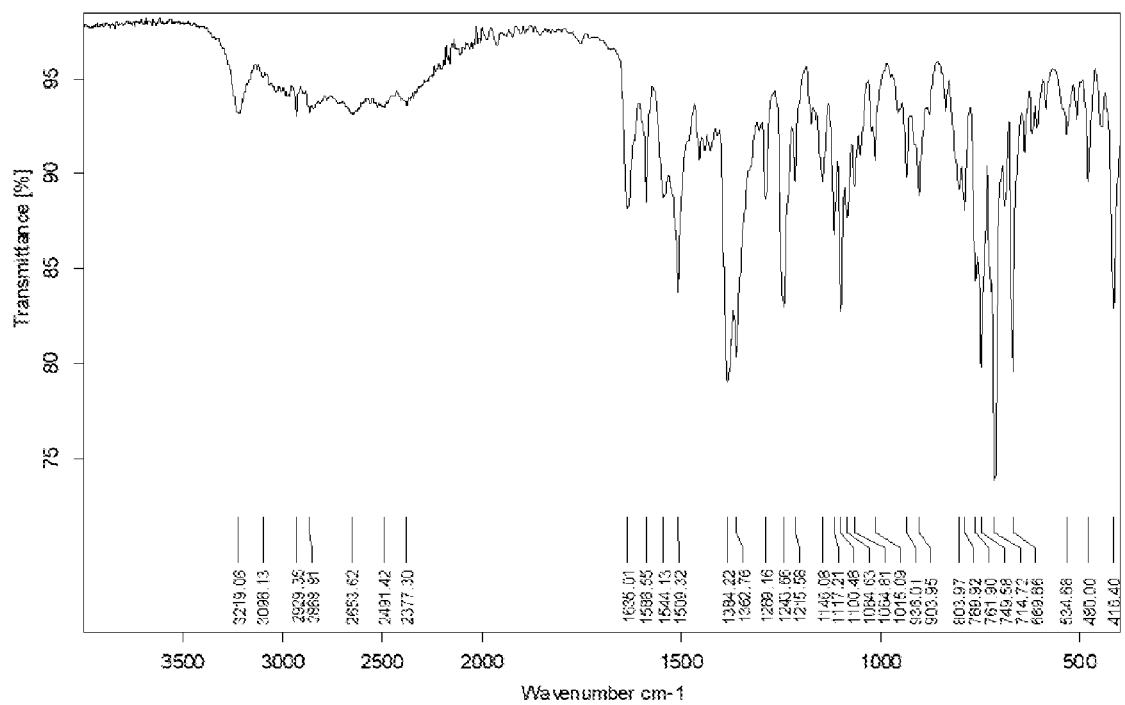
FIG. 12 shows the FT-IR Spectrum of S-pindolol benzoate Pattern 2.
Figure 13:
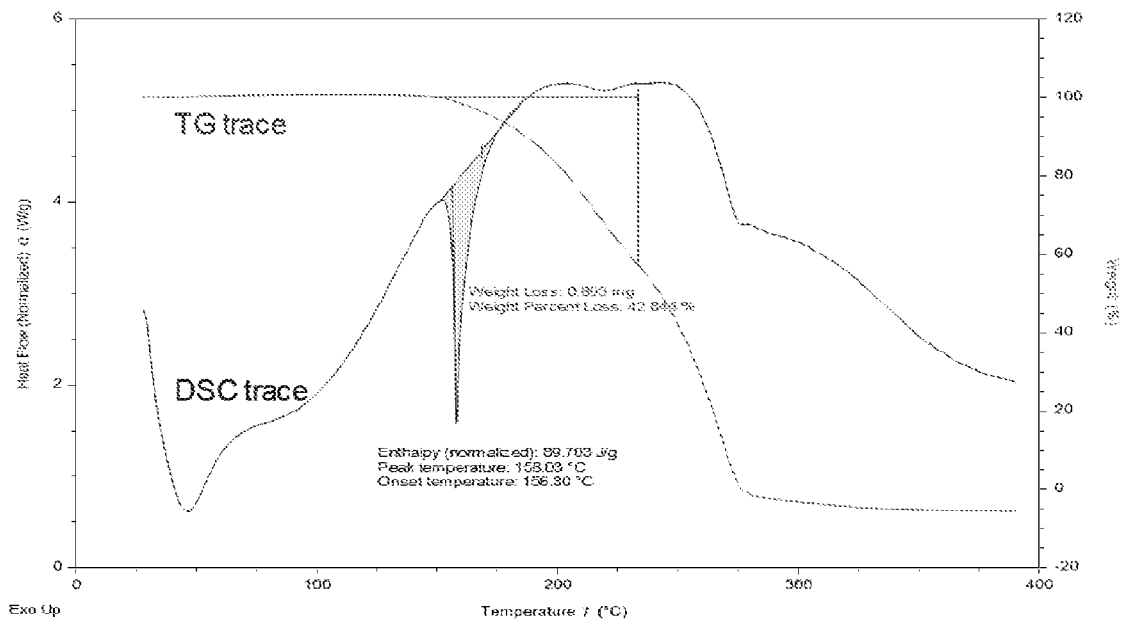
FIG. 13 shows the TG/DSC thermogram of S-pindolol benzoate Pattern 2.
Figure 14:
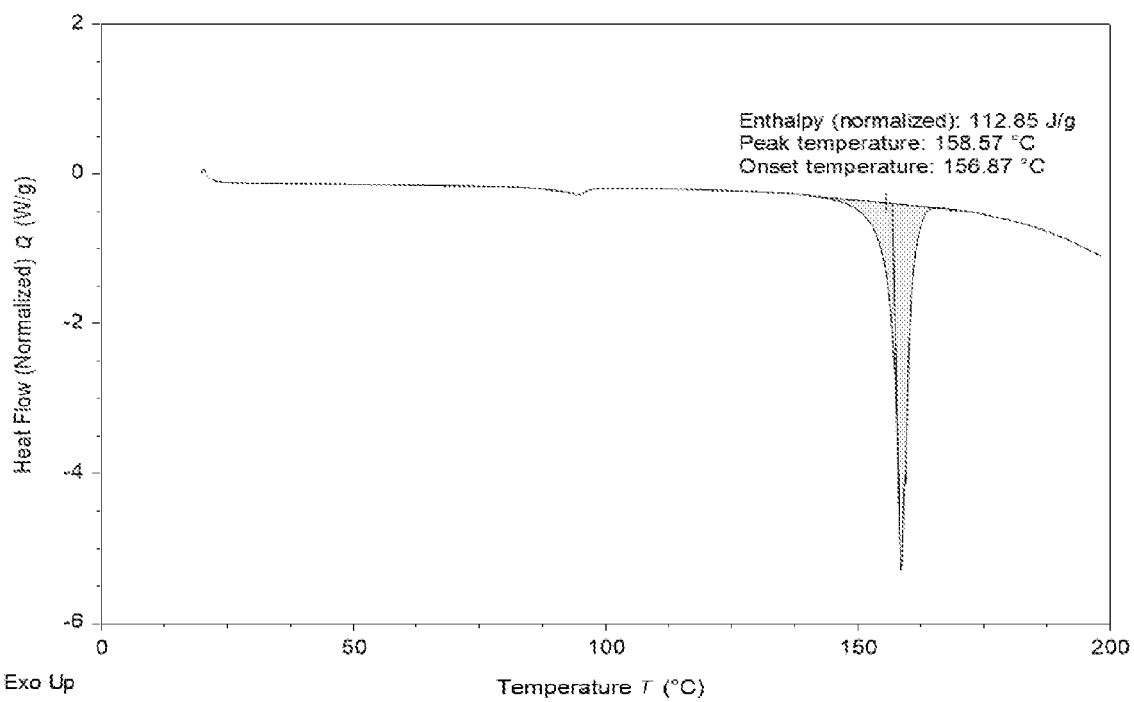
FIG. 14 shows the DSC thermogram of S-pindolol benzoate Pattern 2 (first heating cycle).
Figure 15:
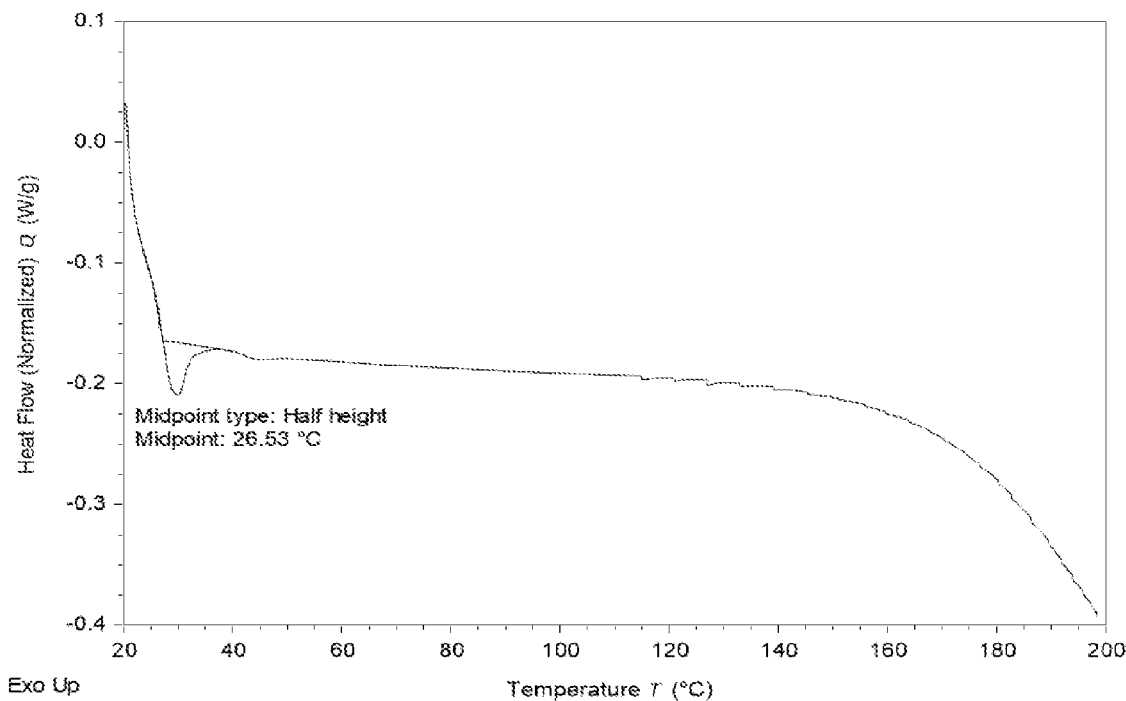
FIG. 15 shows the DSC thermogram of S-pindolol benzoate Pattern 2 (second heating cycle).

FT-IR spectrum matched the supplied structure, see FIG. 12. The following peaks were observed and assigned:
Broad O—H stretch ~3219-2377 cm$^{-1}$
N—H stretch ~3219 cm$^{-1}$
Aromatic C—H stretch ~3098 cm$^{-1}$
Aliphatic C—H stretch ~2929 cm$^{-1}$
Alkene C=C ~1635 cm$^{-1}$ TG and DSC scans of S-pindolol benzoate Pattern 2 are shown in FIGS. 13 to 15. TG/DSC analysis found a 42.8 wt. % mass loss in the TG trace. This was likely due to decomposition. A sharp endothermic event was observed in the DSC trace associated with melting with an onset at 156° C. and peak at 158° C.

DSC analysis found a sharp endothermic event with an onset at 157° C. and peak at 159° C. This corresponds to the melt and matches the TG/DSC data. No events were observed in the cooling cycle. A possible glass transition with a midpoint at 27° C. was observed in the second heating cycle.

Preparation and Characterisation of S-Pindolol Succinate Pattern

S-Pindolol Succinate Pattern 1 Preparation 264.68 mg (1.1 eq.) of succinic acid was added to ca. 500 mg of S-pindolol free base in a scintillation vial. The sample vial which contained the acid was rinsed with 1 mL of THF and the washing was added to the scintillation vial. A further 2 mL of was added and a beige slurry was noted. The scintillation vial was capped and sealed with parafilm and then temperature cycled between ambient temperature and 40° C. oven 4-hour cycles for ca. 72 hours. After 72 hours, the sample was filtered on a Büchner funnel and left to dry on the filter paper for ca. 5 minutes. The material was then placed in a pre-weighed sample vial and dried at 40° C. for ca. 21 hours.

The succinate salt was characterised by XRPD, $^1$H NMR, TG/DSC, DSC, and FT-IR.

S-Pindolol Succinate Pattern 1 Characterisation

XRPD analysis showed S-pindolol succinate was highly crystalline. The pattern (as shown in FIG. 16) was designated as S-pindolol succinate Pattern 1. The 2θ values and peak intensities for S-pindolol succinate Pattern 1 are shown in Table 4 below.

TABLE 4

| Pos. [°2θ] | d-spacing [Å] | Height [cts] | Rel. Int. [%] |
|---|---|---|---|
| 6.0684 | 14.56465 | 654.84 | 7.97 |
| 8.2719 | 10.68914 | 1435.35 | 17.47 |
| 12.1654 | 7.27547 | 1478.35 | 17.99 |
| 12.7849 | 6.92427 | 1490.67 | 18.14 |
| 13.3135 | 6.65056 | 2266.38 | 27.58 |
| 13.5415 | 6.53905 | 608.95 | 7.41 |
| 16.7083 | 5.30615 | 8217.72 | 100.00 |
| 16.9194 | 5.24042 | 1139.91 | 13.87 |
| 18.2804 | 4.85320 | 514.36 | 6.26 |
| 19.5437 | 4.54227 | 1572.79 | 19.14 |
| 21.5220 | 4.12900 | 1265.55 | 15.40 |
| 21.6981 | 4.09589 | 458.95 | 5.58 |
| 21.9519 | 4.04910 | 1034.75 | 12.59 |
| 22.6762 | 3.92139 | 2550.57 | 31.04 |
| 23.3165 | 3.81514 | 801.27 | 9.75 |
| 24.0770 | 3.69631 | 2491.42 | 30.32 |
| 24.2651 | 3.66809 | 887.57 | 10.80 |
| 24.9713 | 3.56593 | 1918.99 | 23.35 |
| 26.8019 | 3.32639 | 791.59 | 9.63 |
| 27.2542 | 3.27220 | 417.74 | 5.08 |

1H NMR found a 1:1 ratio of ACM-001 to succinic acid and 0.04 equiv. of THF.

Figure 17:
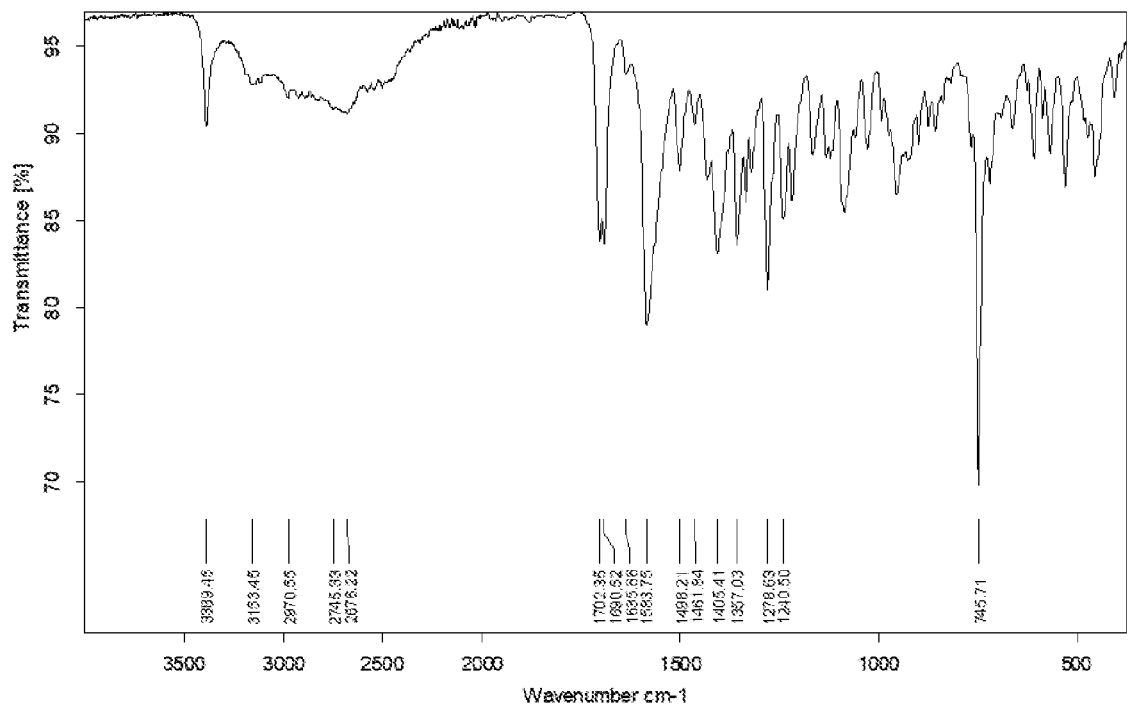
FIG. 17 shows the FT-IR Spectrum of S-pindolol succinate Pattern 1.
Figure 18:
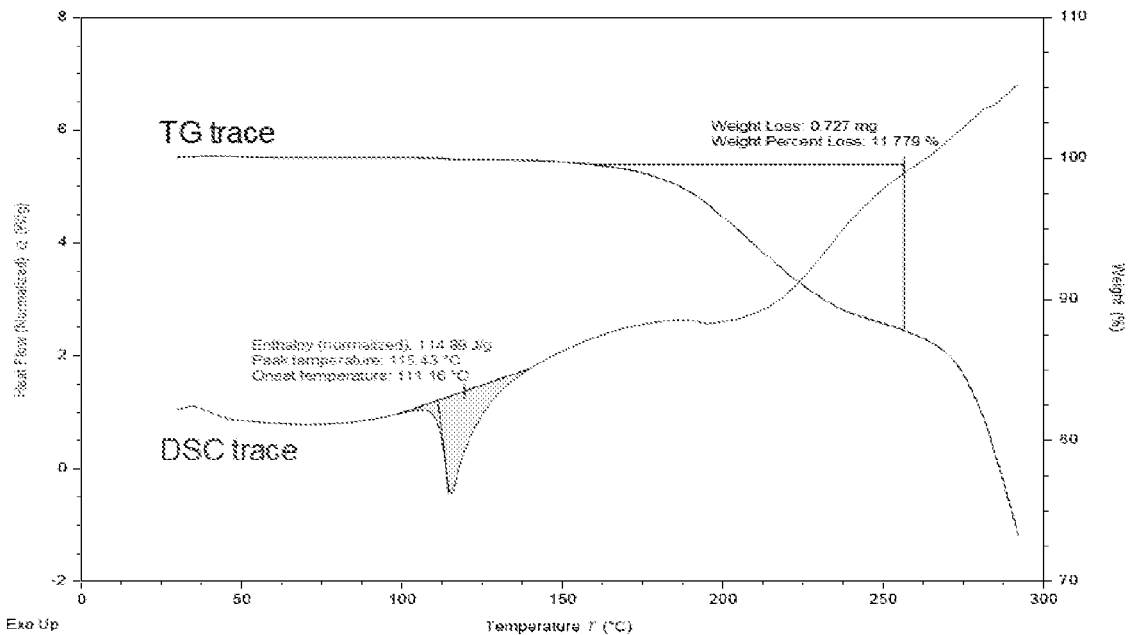
FIG. 18 shows the TG/DSC thermogram of S-pindolol succinate Pattern 1.
Figure 19:
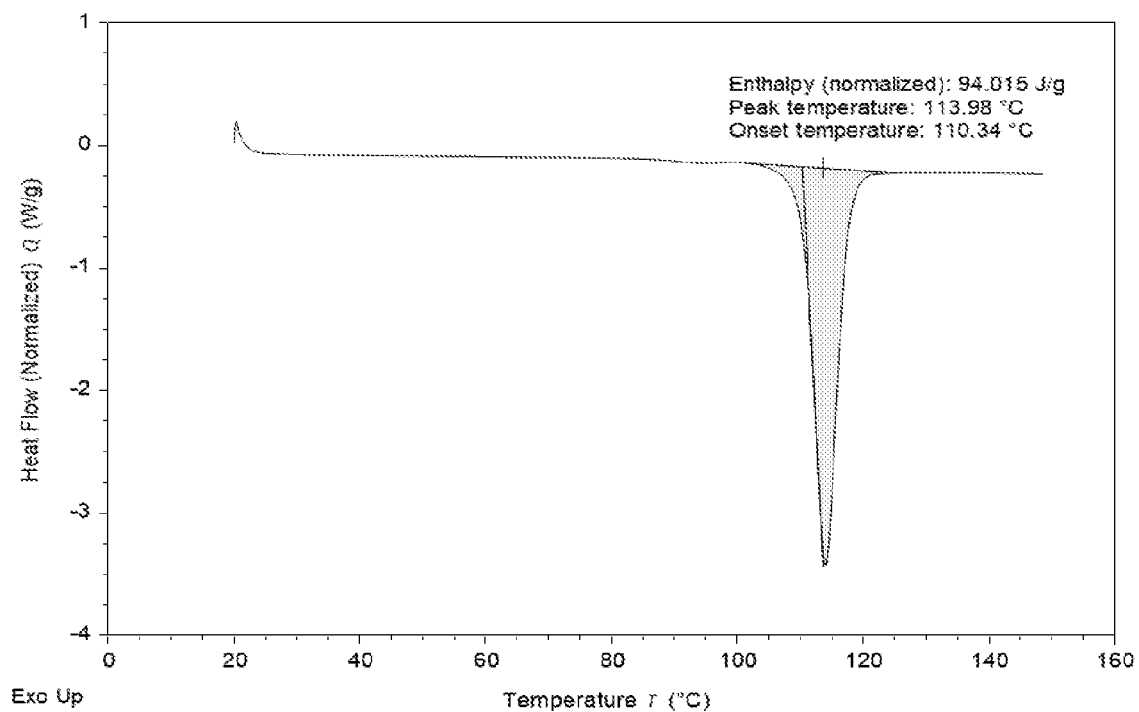
FIG. 19 shows the DSC thermogram of S-pindolol succinate Pattern 1 (first heating cycle).
Figure 20:
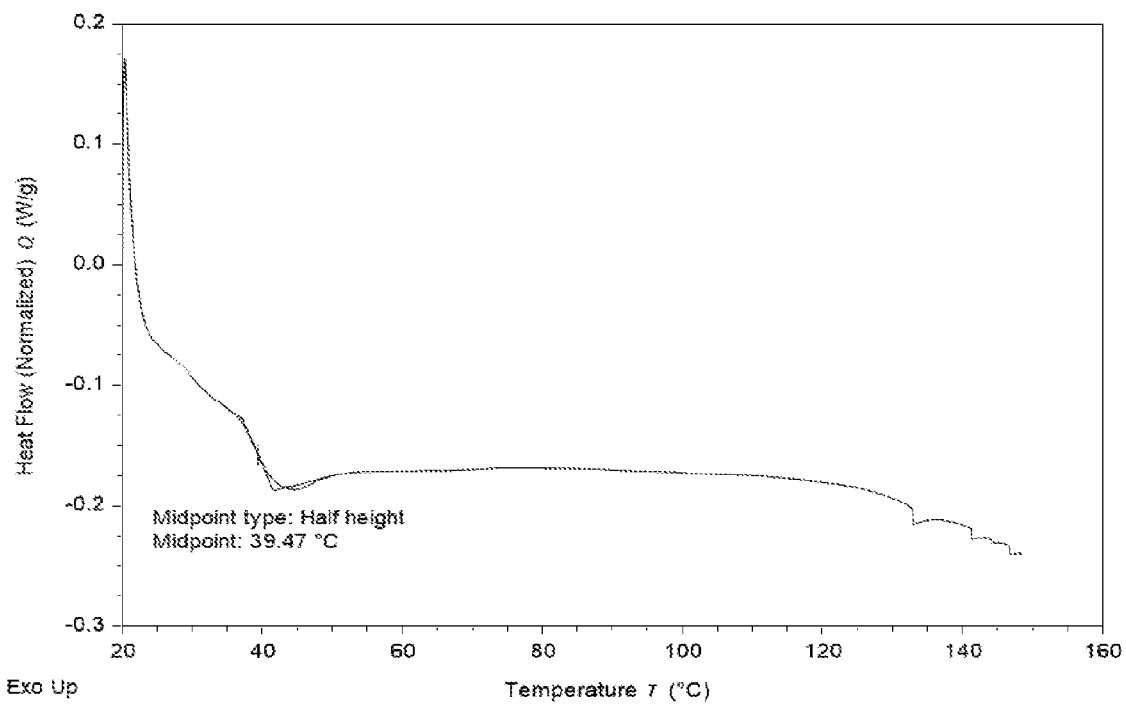
FIG. 20 shows the DSC thermogram of S-pindolol succinate Pattern 1 (second heating cycle).

FT-IR spectrum matched the supplied structure, see FIG. 17. The following peaks were observed and assigned:
Broad O—H stretch ~3389-2676 cm$^{-1}$
N—H stretch ~3389 cm$^{-1}$
Aromatic C—H stretch ~3153 cm$^{-1}$
Aliphatic C—H stretch ~2970 cm$^{-1}$
Alkene C=C ~1690 cm$^{-1}$ TG and DSC scans of S-pindolol succinate Pattern 1 are shown in FIGS. 18 to 20. TG/DSC analysis found a 12% mass loss by TG between 160° C. and 250° C. followed by degradation. This weight loss could be due to degradation but also corresponds to 0.42 eq. succinic acid. An endothermic event was observed in the DSC with an onset of 111° C. and peak of 115° C.

DSC analysis found a sharp endothermic event with an onset at 110° C. and peak at 114° C. This corresponds to the melt and matches the TG/DSC data. No events were observed in the cooling cycle. A glass transition was observed with a midpoint at 39° C. in the second heating cycle.

The stability of S-pindolol succinate Pattern 1 was assessed. The succinate Pattern 1 salt retained its form after storage for 7 days at 60° C. and 40° C./75% RH. No colour changes were observed, purity was maintained and there was no change in the solid form of succinate Pattern 1 after storage at four weeks under all conditions.

The succinate salt was also analysed by DVS. During DVS analysis, succinate Pattern 1 was retained with mass uptake of 0.70 wt % (0.14 eq.) water at 90% RH.

Summary of Characteristics of Salts

A summary of the characteristics of S-pindolol free base Pattern 1, S-pindolol benzoate Pattern 1, S-pindolol benzoate Pattern 2 and S-pindolol succinate Pattern 1 is given in Table 5 below.

TABLE 5

| | Free base Pattern 1 | Benzoate Pattern 1 | Benzoate Pattern 2 | Succinate Pattern 1 |
|---|---|---|---|---|
| XRPD | Highly crystalline | Highly crystalline | Highly crystalline | Highly crystalline |
| $^1$H NMR | Peaks consistent with expected structure, trace impurities possibly due to acetone and hexane | 1:1 ratio. 0.03 eq. ethyl acetate and trace acetic acid. Peak shifting and broad water peak observed | 1:1 ratio. 0.25 wt. % (0.01 eq.) ethyl acetate. Peak shifting and broad water peak observed. | 1:1 ratio, 0.04 eq. THF. Peak shifting and broad water peak observed. |
| FT-IR (ATR) | Matched the supplied structure | Broad water peak, peak shifting indicative of salt formation | Broad water peak, peak shifting indicative of salt formation | Broad water peak, peak shifting indicative of salt formation |

TABLE 5-continued

| | | Free base Pattern 1 | Benzoate Pattern 1 | Benzoate Pattern 2 | Succinate Pattern 1 |
|---|---|---|---|---|---|
| TG/DSC | | Degradation from 200° C. Endothermic events with onset 82° C., peak 84° C. (solid-solid transition), and onset 93° C., peak 95° C. (melting point) | 40% weight loss 150° C.-250° C. (degradation). Endothermic event onset 130° C., peak 135° C. (melting point) | 43% weight loss 150° C.-230° C. (degradation). Endothermic event onset 156° C., peak 158° C. (melting point) | 12% weight loss (degradation) 160° C.-250° C. Endothermic event onset 111° C., peak 115° C. (melting point) |
| DSC | First Heat | Solid-solid transition: onset 83° C., peak 85° C. Melt: onset 93° C., peak 95° C. | Sharp endothermic event: onset 130° C., peak 135° C. | Sharp endothermic event: onset 157° C., peak 159° C. | Sharp endothermic event: onset 110° C., peak 114° C. |
| | Cool | No events | No events | No events | No events |
| | Second Heat | No events | Glass transition: 44° C., Endothermic event: onset 133° C., peak 136° C. | Glass transition: 26° C. | Glass transition: 39° C. |

Example 1

Conclusion

S-pindolol free base was found to be crystalline with an unclear morphology. The thermal properties found were: degradation after 200° C.; a solid-solid transition at 83° C.; and a melt at 93° C. The free base was slightly hygroscopic with an uptake of 0.05 eq. water up to 90% RH.

A salt screen was carried out successfully on S-pindolol. With many counterions, only amorphous products or gums were identified. Crystalline salt forms were identified using fumaric acid, benzoic acid and succinic acid.

All of these crystalline salt forms had higher melting points than the free base and appeared to be anhydrous from the TG/DSC analysis. $^1$H NMR analysis of these samples found stoichiometric amounts of the counterion and peak shifting compared to the free base spectrum which indicated salt formation was successful.

The hemi-fumarate salts were found to interconvert between different polymorphic forms during stability testing and were deemed less desirable salt forms. The fumaric salt products also tended to be coloured.

The benzoate and succinate salts were successfully scaled up for a secondary salt screen. Two polymorphic forms of S-pindolol benzoate (Pattern 1 and Pattern 2) were identified. A single polymorphic form of S-pindolol succinate (Pattern 1) was identified.

S-pindolol benzoate Pattern 1 was found to be a crystalline white solid with a higher melting point than the free base (with an onset at 130° C., while decomposition started around 150° C.).

S-pindolol benzoate Pattern 2 was found to be a crystalline white solid with a higher melting point than the free base (with a melting point onset at 156° C. associated with concurrent decomposition).

S-pindolol succinate Pattern 1 was found to be a crystalline off-white solid with a higher melting point than the free base (with an onset at 111° C., while decomposition started around 160° C.).

The chemical and physical properties of S-pindolol benzoate and S-pindolol succinate are highly advantageous and make them well suited to development for pharmaceutical uses. The pure white colour, better morphology, higher melting point, lower hygroscopicity, and stability determined for S-pindolol benzoate means that this salt is particularly preferred.

Example 2

Polymorphs of S-Pindolol Benzoate

Polymorph Screen

200 μL aliquots of the appropriate solvent were added to ca. 36 mg of amorphous S-pindolol benzoate samples to obtain slurries. The samples were capped, sealed in parafilm and placed in an incubator shaker to temperature cycle (with agitation) between ambient and 40° C. over 4 hour cycles for ca. 72 hours.

After 72 hours, observations were made and the samples were centrifuged within tubes containing filters to isolate the solids and the saturated solutions. The obtained solids were then dried for ca. 24 hours at 40° C. and re-analysed by XRPD to determine the polymorph obtained. The outcome of the polymorph screen is shown in Table 6.

TABLE 6

| Solvent | Pattern obtained |
|---|---|
| 1-butanol | 1 |
| 1-propanol | 1 |
| 1,2-dichloroethane | 1 |
| 1,4-dioxane | 1 |
| 2-ethoxyethanol | 1* |
| 2-methyl THF | 1 |
| 2-methyl-1-propanol | 1 |
| 2-propanol | 1 |
| acetone | 1 |
| acetonitrile | 1 |
| anisole | mixture of 1 and 2 |
| butyl acetate | mixture of 1 and 2 |
| ethanol | 2 |
| ethyl acetate | 1 |
| heptane | 1 |
| isopropyl acetate | 1 |
| methanol | 1 |
| methanol:water (40:60% v/v) | 2[†] |
| methanol:water (80:20% v/v) | 2[†] |
| methanol:water (95:5% v/v) | 2 |
| methylethyl ketone | 2 |
| methylisobutyl ketone | 1 |
| tert-butylmethyl ether | 1 |
| toluene | mixture of 1 and 2 |
| tetrahydrofuran | 2 |
| water | 2 |

*poorly crystalline
[†]additional peaks observed

Most solvents returned Pattern 1. Pattern 2 was obtained from solvents such as methylethyl ketone, ethanol, THF and water. The XRPD pattern of Pattern 2 obtained from methylethyl ketone is shown in FIG. 21.

Competitive Slurries

Figure 22:
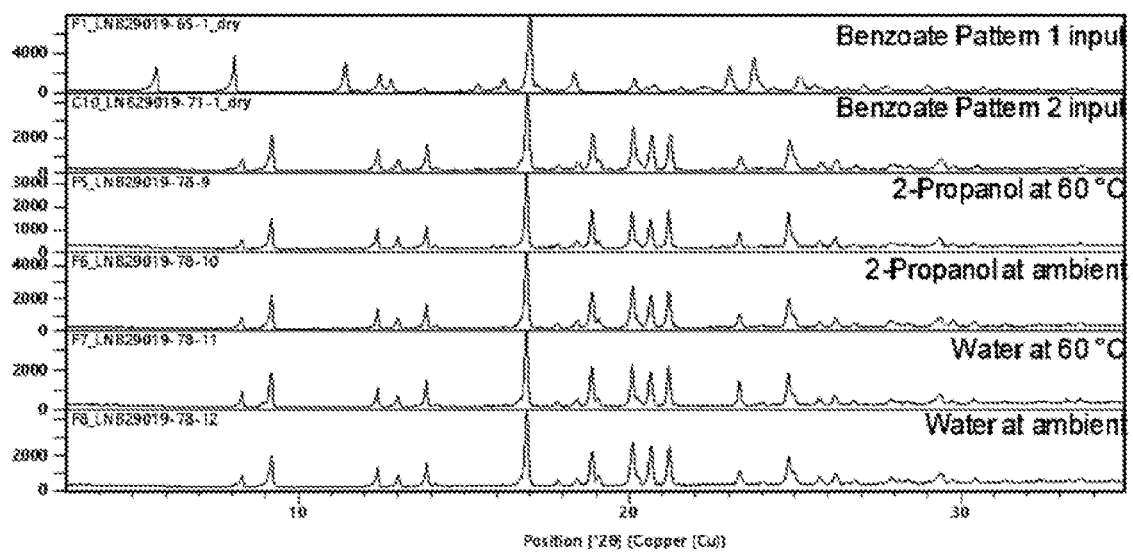
FIG. 22 shows the XRPD diffractograms of samples of S-pindolol benzoate obtained from the competitive slurry experiments.

Four samples containing 10 mg of benzoate Pattern 1 and 10 mg of benzoate Pattern 2 were prepared. 400 μL of 2-propanol was pipetted into two of these samples and 400 μL of water was pipetted into the other two. White slurries were obtained. One slurry in each solvent system was placed in an incubator shaker at 60° C. and the second slurry in each solvent system was placed on a shaker at ambient conditions. After 24 hours, solids were isolated by centrifugation and analysed by XRPD. S-pindolol benzoate Pattern 2 was obtained from all four competitive slurry experiments (as shown in FIG. 22) indicating that Pattern 2 is the thermodynamically stable form.

Summary of Characteristics of S-Pindolol Benzoate Patterns 1 and 2

A summary of the characteristics of S-pindolol benzoate Pattern 1 and S-pindolol benzoate Pattern 2 is given in Table 7 and Table 8 below, where Table 8 includes the results of stability and solubility experiments.

TABLE 7

Summary of characterisation of S-pindolol benzoate Patterns 1 and 2

| | | S-pindolol benzoate Pattern 1 | S-pindolol benzoate Pattern 2 |
|---|---|---|---|
| XRPD | | Highly crystalline, pattern 1 | Highly crystalline, pattern 2 |
| PLM | | Birefringent, 20 μm, plate-like morphology | Birefringent, 10 μm, unclear morphology, agglomeration |
| 1H NMR | | 1:1 ratio. 0.03 eq. ethyl acetate. Peak shifting and broad water peak observed | 1:1 ratio. 0.25 wt. % (0.01 eq.) ethyl acetate, peak shifting and broad water peak observed. |
| FT-IR | | Broad water peak, peak shifting | Broad water peak, peak shifting |
| TG/DSC | | Decomposition from ca. 150° C., 40% weight loss 150° C.-250° C. due to degradation. Endothermic event onset 130° C., peak 135° C. (melting point) | Decomposition from ca. 160° C., 43% weight loss 160° C.-230° C. due to degradation. Endothermic event onset 156° C., peak 158° C. (melting point) |
| DSC | First Heat | Sharp endothermic event: onset 130° C., peak 135° C. | Sharp endothermic event: onset 157° C., peak 159° C. |
| | Cool | No events | No events |
| | Second Heat | Glass transition: 44° C., Endothermic event: onset 133° C., peak 136° C. | Glass transition: 27° C. |
| HPLC purity | | 99.9% relative area | 99.9% relative area |
| Chiral HPLC | | >99.9% ee | 99.4% ee |
| DVS | | Pattern 1 retained, mass uptake of 0.23 wt. % (0.05 eq. water) at 90% RH | Pattern 2 retained, organic solvent loss observed, mass uptake of 0.045 wt. % (0.01 eq. water) at 90% RH |

TABLE 8

Summary of solubility and stability of S-pindolol benzoate Patterns 1 and 2

| | | S-pindolol benzoate Pattern 1 | S-pindolol benzoate Pattern 2 |
|---|---|---|---|
| Thermodynamic solubility | pH 1.2 | Converted to amorphous. Free base concentration: 29.9 mg/mL | Salt disproportionated. Free base concentration: 23.5 mg/mL |
| | pH 4.5 | Converted to amorphous. Free base concentration: 20.1 mg/mL | Pattern 2 retained. Free base concentration: 17.6 mg/mL |
| | pH 6.8 | Pattern 1 retained. Free base concentration: 17.4 mg/mL | Pattern 2 retained. Free base concentration: 9.9 mg/mL |
| | Unbuffered water | N/A | Pattern 2 retained. Free base concentration: 10.3 mg/mL |
| 7-Day Stability | Ambient | Pattern 1 retained. Purity: 99.9% by relative area | Pattern 2 retained. Purity: 99.8% by relative area |
| | 40° C./75% RH | Pattern 1 retained. Purity: 99.8% by relative area | Pattern 2 retained. Purity: 99.9% by relative area |
| | 60° C. | Pattern 1 retained. Purity: 99.8% by relative area | Pattern 2 retained. Purity: 99.9% by relative area |
| | 80° C. | N/A | Pattern 2 retained. Purity: 99.9% by relative area |
| 14-Day Stability | 60° C. | N/A | Pattern 2 retained. Purity: 99.9% by relative area |
| | 40° C./75% RH | | Pattern 2 retained. Purity: 99.9% by relative area |
| | Ambient | | Pattern 2 retained. Purity: 99.9% by relative area |
| | 80° C. | | Pattern 2 retained. Purity: 99.9% by relative area |

Example 2

Conclusion

Most solvent systems yielded S-pindolol benzoate Pattern 1. However, a different pattern, Pattern 2, was recovered from ethanol, methanol/water mixtures, methylethyl ketone, THF and water. Mixtures of Patterns 1 and 2 were observed from anisole, butyl acetate and toluene.

Despite benzoate Pattern 1 being returned from the majority of solvent solubility screen samples, benzoate Pattern 2 was obtained from all polymorph screen experiments that yielded crystalline material and appeared to be the thermodynamic form based on competitive slurry experiments and higher melt onset compared to Pattern 1.

S-pindolol benzoate Pattern 2 was found to be a crystalline white solid with birefringent crystals ca. 10 pm in size with an unclear morphology. Pattern 2 was an anhydrous mono-benzoate salt. The thermal properties of S-pindolol benzoate Pattern 2 improved upon Pattern 1, which supported the theory of Pattern 2 being the thermodynamic form. A higher melting point was obtained with an onset at 156° C. compared to 130° C. for Pattern 1. Decomposition of Pattern 2 occurred at the same temperature as the melt onset. Additionally, a glass transition was observed in the second heating cycle with a midpoint at 27° C. S-pindolol benzoate Pattern 2 was non-hygroscopic with an uptake of 0.045 wt. % (0.01 eq.) water at 90%RH. HPLC analysis found the material to be of 99.9% purity by relative area and an 99.4% ee by chiral HPLC.

7- and 14-day stability testing of S-pindolol benzoate Pattern 2 found that Pattern 2 retained its XRPD pattern and high chemical purity (above 99.8% by relative area) at all stability conditions. Pattern 2 retained its white colour for 7 days at all stability conditions and for 14 days at 60° C. and elevated humidity.

Thermodynamic solubility experiments determined that S-pindolol benzoate Pattern 2 showed fairly high solubility (with free base concentrations of 23.5 mg/mL, 17.6 mg/mL, 9.9 mg/mL, and 10.3 mg/mL) observed in pH 1.2, 4.5, 6.8 buffers and unbuffered water, respectively. S-pindolol benzoate Pattern 2 improved upon the solubility in unbuffered water of the free base which was 1.8 mg/mL The chemical and physical properties of S-pindolol benzoate Patterns 1 and 2 make them both developable salt forms. However, S-pindolol benzoate Pattern 2 was the preferred salt form due to it being the thermodynamic form.

The invention claimed is:

1. A pharmaceutically acceptable acid addition salt of:
   (i) S-pindolol; and
   (ii) benzoic acid,
   wherein the salt is S-pindolol benzoate; and
   wherein:
   the S-pindolol benzoate is in the form of S-pindolol benzoate crystalline polymorph Pattern 1 having an x-ray powder diffraction pattern comprising peaks at 8.1°, 11.4°, 12.5°, 12.8°, 15.4° and 17.0°±0.2°2θ; or
   the S-pindolol benzoate is in the form of S-pindolol benzoate crystalline polymorph Pattern 2 having an x-ray powder diffraction pattern comprising peaks at 16.9°, 18.9° and 20.1°±0.2°2θ.

2. A pharmaceutically acceptable acid addition salt according to claim 1, wherein the S-pindolol benzoate is S-pindolol monobenzoate.

3. A pharmaceutically acceptable acid addition salt according to claim 1, wherein the S-pindolol benzoate is in the form of S-pindolol benzoate crystalline polymorph Pattern 1,
   wherein the x-ray powder diffraction pattern further comprises peaks at 5.7° and 18.4°±0.2°2θ.

4. A pharmaceutically acceptable acid addition salt according to claim 1, wherein the S-pindolol benzoate is in the form of S-pindolol benzoate crystalline polymorph Pattern 2,
   wherein the x-ray powder diffraction pattern further comprises peaks at 9.2°, 13.9° and 20.7°±0.2 2θ.

5. A composition comprising at least 60 wt % of a pharmaceutically acceptable acid addition salt as defined in claim 1, relative to the total weight of the composition.

6. A composition according to claim 5, wherein the composition comprises no more than 30 wt % of R-pindolol or a salt thereof relative to the total weight of the composition.

7. A pharmaceutical composition comprising (a) a pharmaceutically acceptable acid addition salt as defined in claim 1 and (b) a pharmaceutically acceptable excipient, carrier or diluent.

8. A pharmaceutical composition according to claim 7, wherein the pharmaceutical composition is a tablet.

9. A pharmaceutical composition according to claim 7, wherein the pharmaceutical composition comprises less than 1.0 wt % of R-pindolol or a salt thereof.

10. A pharmaceutically acceptable acid addition salt according to claim 1, wherein the S-pindolol benzoate is in the form of S-pindolol benzoate crystalline polymorph Pattern 1 having an x-ray powder diffraction pattern comprising peaks at 8.1°, 11.4°, 12.5°, 12.8°, 15.4° and 17.0°±0.2°2θ.

11. A pharmaceutically acceptable acid addition salt according to claim 1, wherein the S-pindolol benzoate is in the form of S-pindolol benzoate crystalline polymorph Pattern 2 having an x-ray powder diffraction pattern comprising peaks at 16.9°, 18.9° and 20.1°±0.2°2θ.

* * * * *

UNITED STATES PATENT AND TRADEMARK OFFICE
CERTIFICATE OF CORRECTION

PATENT NO. : 12,109,192 B2
APPLICATION NO. : 17/995621
DATED : October 8, 2024
INVENTOR(S) : Robin Chandra Bhattacherjee et al.

It is certified that error appears in the above-identified patent and that said Letters Patent is hereby corrected as shown below:

In the Claims

At Column 24, Line 6, "17.0°±0.2°2θ" should be --17.0° ± 0.2° 2θ--.

At Column 24, Line 10, "20.1°±0.2°2θ" should be --20.1° ± 0.2° 2θ--.

At Column 24, Line 19, "18.4°±0.2°2θ" should be --18.4° ± 0.2° 2θ--.

At Column 24, Line 25, "20.7°±0.2 2θ" should be --20.7° ± 0.2° 2θ--.

At Column 24, Line 46, "17.0°±0.2°2θ" should be --17.0° ± 0.2° 2θ--.

At Column 24, Line 51, "20.1°±0.2°2θ" should be --20.1° ± 0.2° 2θ--.

Signed and Sealed this
Third Day of December, 2024

Katherine Kelly Vidal
*Director of the United States Patent and Trademark Office*